United States Patent
Heil et al.

(10) Patent No.: US 6,444,612 B1
(45) Date of Patent: Sep. 3, 2002

(54) USE OF 5-AMINO-PYRAZOL-DERIVATIVES FOR COMBATING MICRO-ORGANISMS

(75) Inventors: Markus Heil, Leichlingen; Thomas Bretschneider, Lohmar; Hans-Christian Militzer, Odenthal; Astrid Mauler-Machnik, Leichlingen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/763,428

(22) PCT Filed: Aug. 18, 1999

(86) PCT No.: PCT/EP99/06043
§ 371 (c)(1),
(2), (4) Date: Feb. 20, 2001

(87) PCT Pub. No.: WO00/11951
PCT Pub. Date: Mar. 9, 2000

(30) Foreign Application Priority Data

Aug. 26, 1998 (DE) .......................... 198 38 708

(51) Int. Cl.⁷ .................. A01N 46/26; C07D 231/38
(52) U.S. Cl. ................ 504/106; 548/371.4; 548/372.5; 548/376.1
(58) Field of Search .................. 548/368.4, 371.4, 548/372.5, 376.1; 514/407; 504/106

(56) References Cited

U.S. PATENT DOCUMENTS 5,843,978 A * 12/1998 Wernthaler et al. ......... 514/404

FOREIGN PATENT DOCUMENTS

WO 96/21653 7/1996

OTHER PUBLICATIONS

"Preparation of (phenoxy–or 2–pyridyloxyalkylacylamion-!pyrazole derivatives as herbicides and microbicides" retrieved from STN Database accession No. 111:134141 XP002133555 Verbindungen mit RN–121551–00–6 bis 121551–79–9 & JP 63 312773 A (Tokuyama Soda Co., Ltd., Japan) Dec. 21, 1988.

"Preparation of (phenoxyalkanoly amion!pyrazole derivatives as herbicides, fungicides and bactericides" retrieved from STN Database acession No. 107:1706028 XP002133556 Verbindungen mit RN=110731–20–9; 1107631–21–0; 110731–22–1; 110731–24–3; 110731–79–8 –& JP 62 138475 A (Tokuyama Soda Co., LTD., Japan) Jun. 22, 1987.

* cited by examiner

Primary Examiner—Alan L. Rotman
Assistant Examiner—Rita Desai
(74) Attorney, Agent, or Firm—Joseph C. Gil; John E. Mrozinski, Jr.

(57) ABSTRACT

A method of controlling a plant disease caused by a fungus comprising applying a 5-amino-pyrazole of the formula

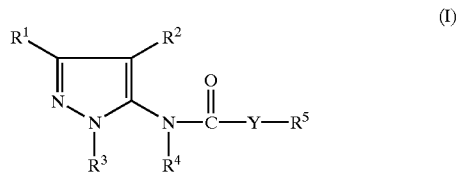

(I)

wherein,

R1, R2, R3, R4, R5 and Y are as defined in the specification.

6 Claims, No Drawings

US 6,444,612 B1

USE OF 5-AMINO-PYRAZOL-DERIVATIVES FOR COMBATING MICRO-ORGANISMS

FIELD OF THE INVENTION

The present invention relates to the use of 5-aminopyrazole derivatives, some of which are known, for controlling undesirable microorganisms.

BACKGROUND OF THE INVENTION

It is already known that certain 5-amino-pyrazole derivatives are suitable for controlling animal pests (cf. WO-A 96-21 653). However, the use of these substances against undesirable microorganisms has hitherto not been described.

SUMMARY OF THE INVENTION

5-Amino-pyrazole derivatives of the formula

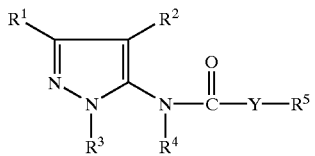

wherein $R^1$, $R^2$, $R^3$, $R^4$, $R^5$ and Y are defined may be used for controlling undesirable microorganisms.

DETAILED DESCRIPTION

It has now been found that 5-amino-pyrazole derivatives of the formula

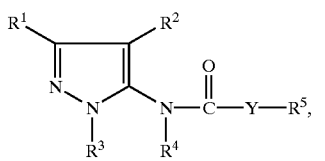

(I)

in which
  $R^1$ represents alkyl, cycloalkyl, alkoxyalkyl or halogenoalkyl,
  $R^2$ represents hydrogen, halogen, cyano, nitro, halogenoalkylthio, aikoxycarbonyl or alkenyloxycarbonyl,
  $R^3$ represents optionally substituted alkyl or optionally substituted cycloalkyl,
  $R^4$ represents hydrogen, alkyl or optionally substituted cycloalkyl,
  Y represents optionally substituted alkanediyl or alkenediyl and
  $R^5$ represents optionally substituted aryl or optionally substituted aryloxy,
  are highly suitable for controlling undesirable microorganisms, both in crop protection and in the protection of materials.

Surprisingly, the 5-amino-pyrazole derivatives of the formula (I) which can be used according to the invention exhibit considerably better microbicidal activity than the constitutionally most similar prior-art substances of the same direction of action.

The formula (I) provides a general definition of the 5-amino-pyrazole derivatives which can be used according to the invention.

$R^1$ preferably represents alkyl having 1 to 4 carbon atoms, cycloalkyl having 3 to 7 carbon atoms, alkoxyalkyl having 1 to 4 carbon atoms in the alkyl moiety and 1 to 4 carbon atoms in the alkoxy moiety or represents halogenoalkyl having 1 to 4 carbon atoms and 1 to 5 identical or different halogen atoms, $R^2$ preferably represents hydrogen, fluorine, chlorine, bromine, cyano, nitro, trifluoromethylthio, difluoromethylthio, alkoxycarbonyl having 1 to 4 carbon atoms in the alkoxy moiety or represents alkenyloxycarbonyl having 2 to 4 carbon atoms in the alkenyloxy moiety, $R^3$ preferably represents optionally cyano-substituted alkyl having 1 to 4 carbon atoms or represents cycloalkyl having 3 to 6 carbon atoms which is optionally mono- to trisubstituted by identical or different substituents from the group consisting of halogen and alkyl having 1 to 4 carbon atoms, $R^4$ preferably represents hydrogen, alkyl having 1 to 4 carbon atoms or represents cycloalkyl having 3 to 6 carbon atoms which is optionally mono- to trisubstituted by identical or different substituents from the group consisting of halogen and alkyl having 1 to 4 carbon atoms, Y preferably represents alkanediyl having 1 to 4 carbon atoms which is optionally mono- or disubstituted by halogen and/or cycloalkyl having 3 to 6 carbon atoms and $R^5$ preferably represents phenyl or phenoxy, where each of these radicals may be mono- to tetrasubstituted by identical or different substituents from the group consisting of halogen, nitro, cyano, $C_1$–$C_{12}$-alkyl, $C_1$–$C_{12}$-alkoxy, $C_1$–$C_{12}$-alkylthio, $C_1$–$C_{12}$-halogenoalkyl, $C_1$–$C_{12}$-halogenoalkoxy, $C_1$–$C_{12}$-halogenoalkylthio, $C_2$–$C_{12}$-alkenyl, $C_1$–$C_4$-alkoxy-$C_2$–$C_{12}$-alkenyl, $C_1$–$C_4$-alkylthio-$C_2$–$C_{12}$-alkenyl, $C_2$–$C_{12}$-halogenoalkenyl, carboxyl, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkenyloximinoalkyl having 2 to 4 carbon atoms in the alkenyloxy moiety and 1 to 4 carbon atoms in the alkyl moiety, alkylcarbonyl having 1 to 6 carbon atoms in the alkyl moiety, alkylcarbonyloxy having 1 to 4 carbon atoms in the alkyl moiety, or by phenyl, phenoxy, phenylthio, benzyl, benzyloxy and/or pyridyloxy, where the six lastmentioned radicals for their part may be mono- to trisubstituted by identical or different radicals from the group consisting of halogen, nitro, cyano, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio, or $R^5$ preferably represents phenyl or phenoxy, where each of these radicals is monosubstituted by a radical of the formula

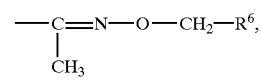

in which
  $R^6$ represents phenyl or pyridyl, where each of these radicals may be mono- to trisubstituted by identical or different substituents from the group consisting of halogen, alkyl having 1 to 4 carbon atoms, halogenoalkyl having 1 to 4 carbon atoms and 1 to 5 identical or different halogen atoms and halogenoalkoxy having 1 to 4 carbon atoms and 1 to 5 identical or different halogen atoms, or $R^5$ represents phenyl or phenoxy, where each of these radicals is monosubstituted by a radical of the formula

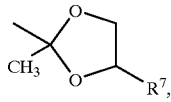

in which $R^7$ represents alkyl having 1 to 6 carbon atoms or alkoxyalkyl having 1 to 6 carbon atoms in the alkoxy moiety and 1 to 6 carbon atoms in the alkyl moiety, or $R^5$ represents phenyl or phenoxy, where each of these radicals is monosubstituted by a radical of the formula

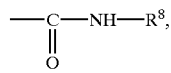

in which $R^8$ represents alkyl having 1 to 6 carbon atoms, benzyl or pyridylmethyl, where the two lastmentioned radicals may be mono- to trisubstituted by identical or different substituents from the group consisting of halogen, alkyl having 1 to 4 carbon atoms, halogenoalkyl having 1 to 4 carbon atoms and 1 to 5 identical or different halogen atoms and halogenoalkoxy having 1 to 4 carbon atoms and 1 to 5 identical or different halogen atoms, or $R^5$ represents a radical of the formula

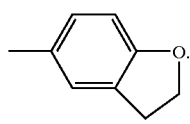

$R^1$ particularly preferably represents methyl, ethyl, n- or i-propyl or n-, i-, s- or t-butyl, cyclopropyl, represents methoxymethyl, ethoxymethyl, methoxyethyl, ethoxyethyl, trifluoromethyl, difluoromethyl, fluoromethyl, 1-chloro-1-ethyl or 1-fluoro- 1-ethyl.

$R^2$ particularly preferably represents hydrogen, fluorine, chlorine, bromine, cyano, nitro, trifluoromethylthio, difluoromethylthio, methoxycarbonyl, ethoxycarbonyl, n- or i-propoxycarbonyl, n-, i-, s- or t-butoxycarbonyl or allyloxycarbonyl.

$R^3$ particularly preferably represents methyl, ethyl, n- or i-propyl, n-, i-, s- or t-butyl, or represents 2-cyanoethyl, cyclopropyl, cyclopentyl or cyclohexyl, where the three lastmentioned radicals may be mono- to trisubstituted by identical or different radicals from the group consisting of fluorine, chlorine, methyl and ethyl.

$R^4$ particularly preferably represents hydrogen, methyl, ethyl, n-propyl, isopropyl, n-, i-, s- or t-butyl or represents cyclopropyl, cyclopentyl or cyclohexyl, where the three lastmentioned radicals may be mono- to trisubstituted by identical or different substituents from the group consisting of fluorine, chorine, methyl and ethyl.

Y particularly preferably represents a grouping of the formula

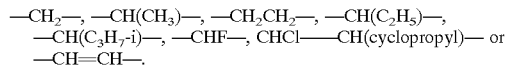

$R^5$ particularly preferably represents phenyl or phenoxy, where each of these radicals may be mono- to tetrasubstituted by identical or different substituents from the group consisting of fluorine, chlorine, bromine, nitro, cyano, methyl, ethyl, n- and i-propyl, n-, i-, s- and t-butyl, methoxy, ethoxy, n- and i-propoxy, n-, i-, s- and t-butoxy, methylthio, trifluoromethyl, difluoromethyl, trifluoromethoxy, difluoromethoxy, trifluoromethylthio, difluoromethyithio, carboxyl, hydroximinoalkyl having 1 or 2 carbon atoms in the alkyl moiety, alkoximinoalkyl having 1 to 4 carbon atoms in the alkoxy moiety and 1 or 2 carbon atoms in the alkyl moiety, alkenyloximninoalkyl having 2 to 4 carbon atoms in the alkenyloxy moiety and 1 or 2 carbon atoms in the alkyl moiety, alkylcarbonyl having 1 to 4 carbon atoms in the alkyl moiety, alkylcarbonyloxy having 1 to 4 carbon atoms in the alkyl moiety, or by phenyl, phenoxy, phenylthio, benzyl, benzyloxy and/or pyridyloxy, where the six lastmentioned radicals for their part may be mono- to trisubstituted by identical or different substituents from the group consisting of fluorine, chlorine, bromine, nitro, cyano, methyl, ethyl, tert-butyl, methylthio, methoxy, ethoxy, n- or i-propoxy or n-, i-, s- or t-butoxy, trifluoromethyl, trifluoromethoxy, difluoromethoxy and trifluoromethylthio, or $R^5$ represents phenyl or phenoxy, where each of these radicals is monosubstituted by a radical of the formula

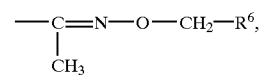

in which $R^6$ represents phenyl or pyridyl, where each of these radicals may be mono- to trisubstituted by identical or different substituents from the group consisting of fluorine, chlorine, bromine, methyl, ethyl, n-propyl, halogenoalkyl having 1 or 2 carbon atoms and 1 to 3 fluorine-, chlorine- and/or bromine atoms and halogenoalkoxy having 1 or 2 carbon atoms and 1 to 3 fluorine, chlorine and/or bromine atoms, or $R^5$ represents phenyl or phenoxy, where each of these radicals is monosubstituted by a radical of the formula

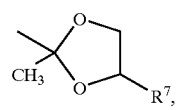

in which $R^7$ represents alkyl having 1 to 4 carbon atoms or alkoxyalkyl having 1 to 4 carbon atoms in the alkoxy moiety and 1 to 4 carbon atoms in the alkyl moiety, or $R^5$ represents phenyl or phenoxy, where each of these radicals is monosubstituted by a radical of the formula

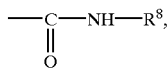

in which

R$^8$ represents alkyl having 1 to 4 carbon atoms, benzyl or pyridylmethyl, where the two lastmentioned radicals may be mono- to trisubstituted by identical or different substituents from the group consisting of fluorine, chlorine, bromine, methyl, ethyl, n-propyl, halogenoalkyl having 1 or 2 carbon atoms and 1 to 3 fluorine, chlorine and/or bromine atoms and halogenoalkoxy having 1 or 2 carbon atoms and 1 to 3 fluorine, chlorine and/or bromine atoms, or R$^5$ represents a radical of the formula

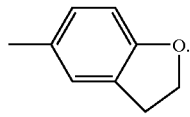

R$^1$ very particularly preferably represents methyl, ethyl, i-propyl, tert-butyl, methoxymethyl, 1-chlorine-1-ethyl, 1-fluorine-1-ethyl or cyclopropyl.

R$^2$ very particularly preferably represents hydrogen, chlorine, bromine, cyano, nitro, methoxycarbonyl, ethoxycarbonyl or allyloxycarbonyl.

R$^3$ very particularly preferably represents methyl, ethyl, i-propyl, tert-butyl, cyclopropyl or 2-cyanoethyl.

R$^4$ very particularly preferably represents hydrogen, methyl, ethyl, i-propyl or cyclopropyl.

Y very particularly preferably represents a grouping of the formula

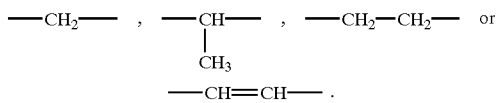

R$^5$ very particularly preferably represents phenyl or phenoxy, where each of these radicals may be mono- to trisubstituted by identical or different substituents from the group consisting of fluorine, chlorine, bromine, nitro, cyano, methyl, ethyl, n- and i-propyl, n-, i-, s- and t-butyl, methoxy, ethoxy, n- and i-propoxy, n-, i-, s- and t-butoxy, methylthio,. trifluoromethyl, trifluoromethoxy, difluoromethoxy, trifluoromethylthio, carboxyl, hydroximinomethyl, hydroximinoethyl, alkoximinoalkyl having 1 to 4 carbon atoms in the alkoxy moiety and 1 or 2 carbon atoms in the alkyl moiety, allyloximinoalkyl having 1 or 2 carbon atoms in the alkyl moiety, methylcarbonyl, ethylcarbonyl, methylcarbonyloxy, ethylcarbonyloxy, or by phenyl, phenoxy, phenylthio, benzyl, benzyloxy and/or pyridyloxy, where the six lastmentioned radicals for their part may be mono- to trisubstituted by identical or different substituents from the group consisting of fluorine, chlorine, bromine, nitro, cyano, methyl, tert-butyl, methylthio, methoxy, ethoxy, n- and i-propoxy, n-, i-, s- and t-butoxy, trifluoromethyl, trifluoromethoxy, difluoromethoxy and trifluoromethylthio, or R$^5$ represents phenyl or phenoxy, where each of these radicals is monosubstituted by a radical of the formula

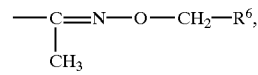

in which

R$^6$ represents phenyl or pyridyl, where each of these radicals may be mono- to trisubstituted by identical or different substituents from the group consisting of fluorine, chlorine, bromine, methyl, ethyl, trifluoromethyl and trifluoromethoxy, or R$^5$ represents phenyl or phenoxy, where each of these radicals is monosubstituted by a radical of the formula

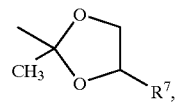

in which

R$^7$ represents methyl, ethyl, n-propyl or alkoxyalkyl having 1 to 4 carbon atoms in the alkoxy moiety and 1 or 2 carbon atoms in the alkyl moiety, or R$^5$ represents phenyl or phenoxy, where each of these radicals is monosubstituted by a radical of the formula

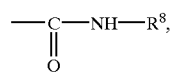

in which

R$^8$ represents methyl, ethyl, n-propyl, benzyl or pyridylmethyl, where the two lastmentioned radicals may be mono- to trisubstituted by identical or different substituents from the group consisting of fluorine, chlorine, bromine, methyl, ethyl, n-propyl, trifluoromethyl and trifluoromethoxy, or R$^5$ represents a radical of the formula

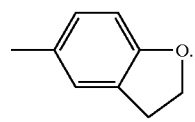

The given definitions of substituents can be combined with one another as desired. Moreover, individual definitions of substituents may also apply.

Some of the 5-amino-pyrazole derivatives of the formula (I) which can be used according to the invention are known (cf. WO-A 96-21 653).

The 5-amino-pyrazole derivatives of the formula

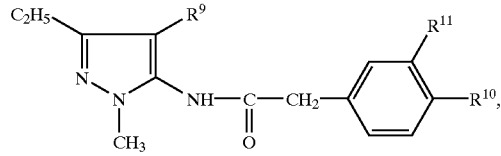
(Ia)

in which
a) $R^9$ represents chlorine,
   $R^{10}$ represents the radical

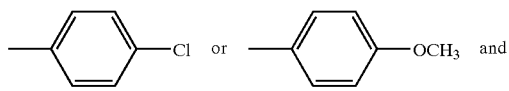
and $R^{11}$ represents hydrogen,
or
b) $R^9$ and $R^{11}$ each represent hydrogen and
   $R^{10}$ represents the radical

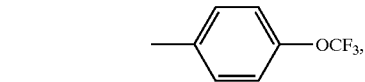

or
c) $R^9$ represents hydrogen, chlorine, cyano or ethoxycarbonyl,
   $R^{10}$ represents hydrogen and
   $R^{11}$ represents chlorine, bromine, methoxy or trifluoromethyl, are novel.

The 5-amino-pyrazole derivatives of the formula (Ia) can be prepared by
a) reacting 5-aminopyrazoles of the formula

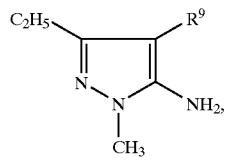
(II)

in which
$R^9$ is as defined above
with acyl halides of the formula

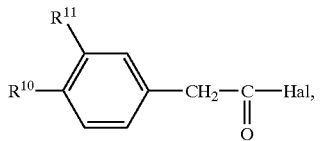
(III)

in which
$R^{10}$ and $R^{11}$ are as defined above and
Hal represents chlorine or bromine,
if appropriate in the presence of an acid binder and if appropriate in the presence of a diluent, or b) reacting 5-amino-pyrazole derivatives of the formula

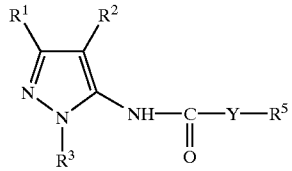
(Ib)

in which
$R^{10}$ and $R^{11}$ are as defined above,
with a chlorinating agent, if appropriate in the presence of a diluent and if appropriate in the presence of a catalyst.

Using the above process, it is also possible to prepare the other 5-amino-pyrazole derivatives of the formula (I).

The 5-amino-pyrazole derivatives of the formula (Ic)

in which the substituents $R^1$, $R^2$, $R^3$, $R^5$ and Y have the meanings given in Table 1 below are likewise novel.

TABLE 1

| $R^1$ | $R^2$ | $R^3$ | —Y—$R^5$ |
|---|---|---|---|
| —CH$_3$ | H | —CH$_3$ | —CH$_2$—⟨C$_6$H$_4$⟩—C(CH$_3$)$_3$ |
| —CH$_3$ | H | —CH$_3$ | —CH$_2$—O—⟨C$_6$H$_3$(CH$_3$)$_2$⟩ |

TABLE 1-continued

| R¹ | R² | R³ | —Y—R⁵ |
|---|---|---|---|
| —CH₃ | Br | —CH₃ | —CH₂—O—(2,3-dimethyl-4-bromophenyl) |
| —CH₃ | Cl | —CH₃ | —CH₂—(4-t-C₄H₉-phenyl) |
| C₂H₅ | —CN | —CH₃ | —CH₂—(2,3-dihydrobenzofuran-5-yl) |
| C₂H₅ | Cl | —CH₃ | —CH₂—(2,3,5-trimethylphenyl) |
| C₂H₅ | —CN | —CH₃ | —CH₂—(4-(3-chloro-5-trifluoromethyl-2-pyridyloxy)phenyl) |
| C₂H₅ | —COOC₂H₅ | —CH₃ | —CH₂—(4-(benzyloxy)phenyl) |
| C₂H₅ | H | —CH₃ | —CH₂—(4-bromophenyl) |
| C₂H₅ | —COOC₂H₅ | —CH₃ | —CH=CH—(4-(4-cyanophenoxy)phenyl) |
| C₂H₅ | —COOC₂H₅ | —CH₃ | —CH=CH—(4-(4-nitrophenoxy)phenyl) |
| C₂H₅ | —CN | —CH₃ | —CH=CH—(4-(4-nitrophenoxy)phenyl) |
| cyclopropyl | H | —CH₃ | —CH—(4-(4-cyanophenoxy)phenyl) |
| cyclopropyl | Cl | —CH₃ | —CH—(4-(4-cyanophenoxy)phenyl) |
| C₂H₅ | —COOC₂H₅ | —CH₃ | —CH₂—(3-phenoxyphenyl) |

TABLE 1-continued
| R¹ | R² | R³ | —Y—R⁵ |
|---|---|---|---|
| —CH₃ | Cl | —CH₃ | 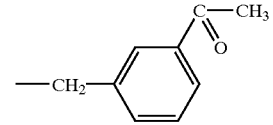 |
| —CH₃ | H | —CH₂—CH₂—CN | 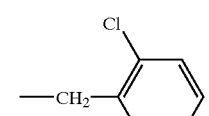 |
| —CH₃ | —CN | —CH₃ | 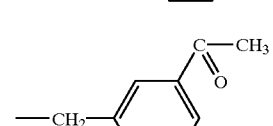 |
| C₂H₅ | —CN | —CH₃ | 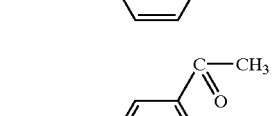 |
| —CH₃ | —COO—CH₃ | —CH₃ | 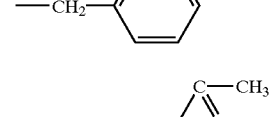 |
| —CH₃ | Cl | —CH₃ | 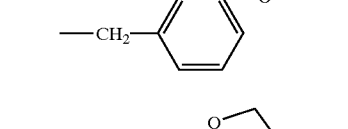 |
| —CH₃ | Cl | —CH₃ | 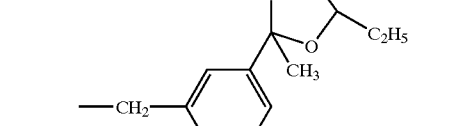 |
| —CH₃ | —CN | —CH₃ | 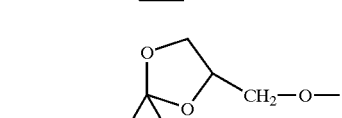 |
| C₂H₅ | —CN | —CH₃ | 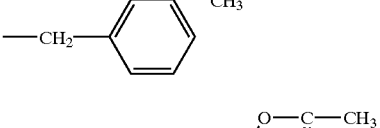 |
| —CH₃ | H | —CH₃ | 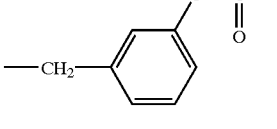 |

TABLE 1-continued
| R¹ | R² | R³ | —Y—R⁵ |
|---|---|---|---|
| —CH₃ | Cl | —CH₃ | 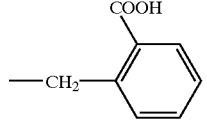 |
| —CH₃ | Cl | —CH₃ | 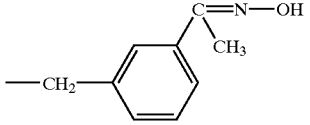 |
| —CH₃ | Cl | —CH₃ | 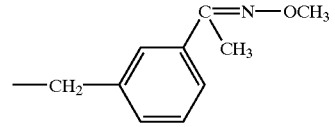 |
| —CH₃ | Cl | —CH₃ | 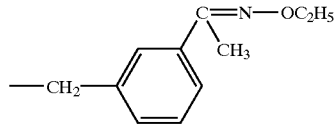 |
| —CH₃ | Cl | —CH₃ | 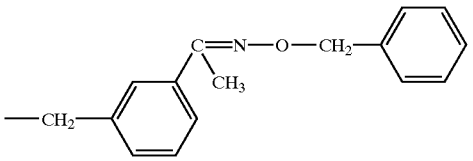 |
| —CH₃ | Cl | —CH₃ | 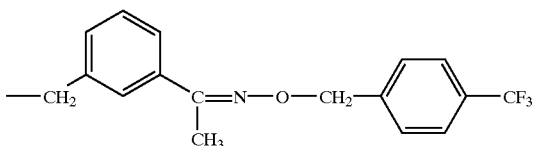 |
| —CH₃ | Cl | —CH₃ | 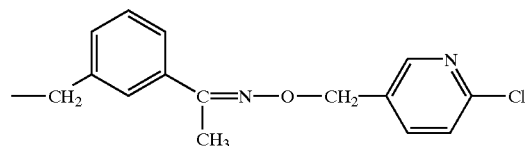 |
| —CH₃ | Cl | —CH₃ | 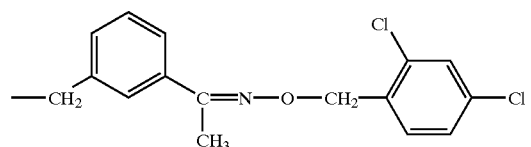 |
| —CH₃ | Cl | —CH₃ | 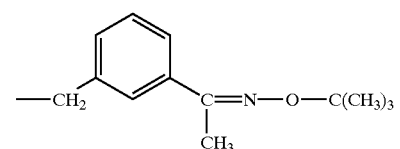 |
| —CH₃ | Cl | —CH₃ | 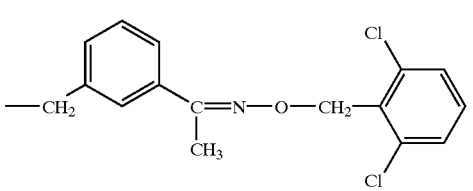 |

TABLE 1-continued

| R¹ | R² | R³ | —Y—R⁵ |
|---|---|---|---|
| —CH₃ | Cl | —CH₃ | —CH₂—C(CH₃)=N—O—CH₂—CH=CH₂ (phenyl at meta position on C) |
| —CH₃ | Cl | —CH₃ | —CH₂—(2-phenyl)—C(=O)—NH—C₃H₇-n |
| —CH₃ | Cl | —CH₃ | —CH₂—(2-phenyl)—C(=O)—NH—CH₂—(6-chloropyridin-3-yl) |
| —CH₃ | —COO—CH₃ | —CH₃ | —CH₂—(3-bromophenyl) |
| C₂H₅ | —CN | —CH₃ | —CH₂—(2,4,6-trimethylphenyl, with 3-CH₃) |
| —CH₃ | —CN | —CH₃ | —CH₂—(2,3,5,6-tetramethylphenyl) |
| —CH₃ | Cl | —CH₃ | —CH₂—(2-(2,4-dimethylphenoxy)phenyl) |
| —CH₃ | Cl | —CH₃ | —CH₂—(4-biphenyl) |

TABLE 1-continued
| R¹ | R² | R³ | —Y—R⁵ |
|---|---|---|---|
| —CH₃ | Cl | —CH₃ | 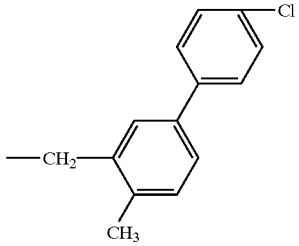 |
| —CH₃ | Cl | —CH₃ | 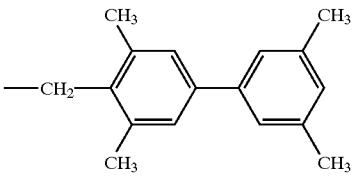 |
| —CH₃ | Cl | —CH₃ | 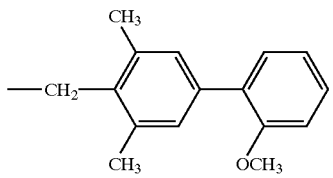 |
| —CH₃ | Cl | —CH₃ | 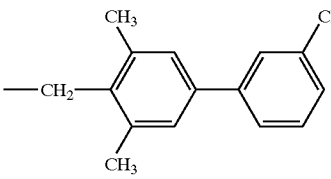 |
| —CH₃ | Cl | —CH₃ | 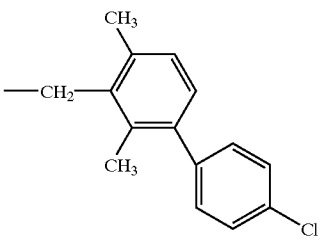 |
| —CH₃ | Cl | —CH₃ | 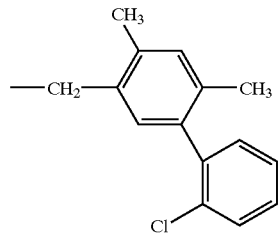 |
| —CH₃ | Cl | —CH₃ | 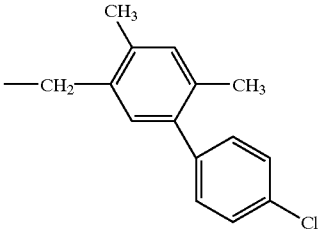 |

TABLE 1-continued

| R¹ | R² | R³ | —Y—R⁵ |
|---|---|---|---|
| —CH₃ | Cl | —CH₃ | —CH₂—(2,3,6-trimethyl-C₆H)—(4-chlorophenyl) |
| —CH₃ | Cl | —CH₃ | —CH₂—(2-CF₃-3,5,6-trifluorophenyl) |
| —CH₃ | —CN | —CH₃ | —CH₂—(phenyl)—O—(2,4-dimethylphenyl) |
| —CH₃ | —CN | —CH₃ | —CH₂—(4-biphenylyl) |
| —CH₃ | —CN | —CH₃ | —CH₂—(3-methyl-4-methylphenyl)—(4-chlorophenyl) |
| —CH₃ | —CN | —CH₃ | —CH₂—(3,5-dimethyl-4-yl)—(3,5-dimethylphenyl) |
| —CH₃ | —CN | —CH₃ | —CH₂—(3,5-dimethylphenyl)—(2-methoxyphenyl) |
| —CH₃ | —CN | —CH₃ | —CH₂—(3,5-dimethylphenyl)—(4-chlorophenyl) |

TABLE 1-continued

| R¹ | R² | R³ | —Y—R⁵ |
|---|---|---|---|
| —CH₃ | —CN | —CH₃ | —CH₂— 3,5-dimethyl-4-yl-(3'-chlorobiphenyl) |
| —CH₃ | —CN | —CH₃ | —CH₂— 2,4-dimethyl-3-yl-(4'-chlorobiphenyl) |
| —CH₃ | —CN | —CH₃ | —CH₂— 2,4-dimethyl-6-(2'-chlorophenyl)-3-yl |
| —CH₃ | —CN | —CH₃ | —CH₂— 2,4-dimethyl-5-(4'-chlorophenyl)phenyl |
| —CH₃ | —CN | —CH₃ | —CH₂— 2,4,6-trimethyl-3-(4'-chlorophenyl)phenyl |
| —CH₃ | —CN | —CH₃ | —CH₂— 2,3,5-trifluoro-6-trifluoromethylphenyl |

TABLE 1-continued

| R¹ | R² | R³ | —Y—R⁵ |
|---|---|---|---|
| —C₂H₅ | —CN | —CH₃ | —CH₂— (2-ethyl-3-methylphenyl)—O—(2,4-dimethylphenyl) |
| —C₂H₅ | —CN | —CH₃ | —CH₂—(4-biphenyl) |
| —C₂H₅ | —CN | —CH₃ | —CH₂—(4-methyl-3-(4-chlorophenyl)phenyl) |
| —C₂H₅ | —CN | —CH₃ | —CH₂—(3,5-dimethyl-4-(3,5-dimethylphenyl)phenyl) |
| —C₂H₅ | —CN | —CH₃ | —CH₂—(3,5-dimethyl-4-(2-methoxyphenyl)phenyl) |
| —C₂H₅ | —CN | —CH₃ | —CH₂—(3,5-dimethyl-4-(4-chlorophenyl)phenyl) |
| —C₂H₅ | —CN | —CH₃ | —CH₂—(3,5-dimethyl-4-(3-chlorophenyl)phenyl) |

TABLE 1-continued

| R¹ | R² | R³ | —Y—R⁵ |
|---|---|---|---|
| —C₂H₅ | —CN | —CH₃ | 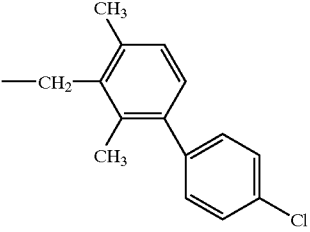 |
| —C₂H₅ | —CN | —CH₃ | 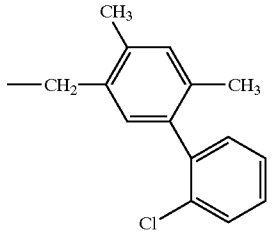 |
| —C₂H₅ | —CN | —CH₃ | 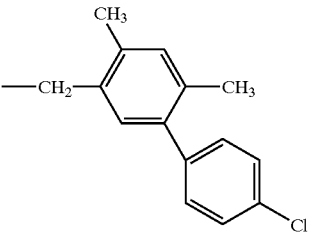 |
| —C₂H₅ | —CN | —CH₃ | 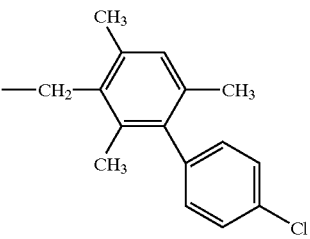 |
| —C₂H₅ | —CN | —CH₃ | 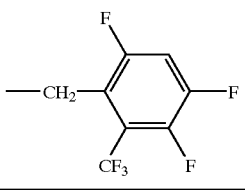 |

The 5-amino-pyrazole derivatives listed in Table 1 are likewise prepared by the processes mentioned above.

Using 5-amino-3-ethyl-4-ethoxycarbonyl-1-methyl-pyrazole and (3-chlorophenyl)-acetyl chloride as starting materials, the course of the process (a) according to the invention can be illustrated by the equation below.

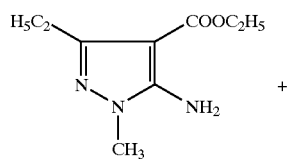

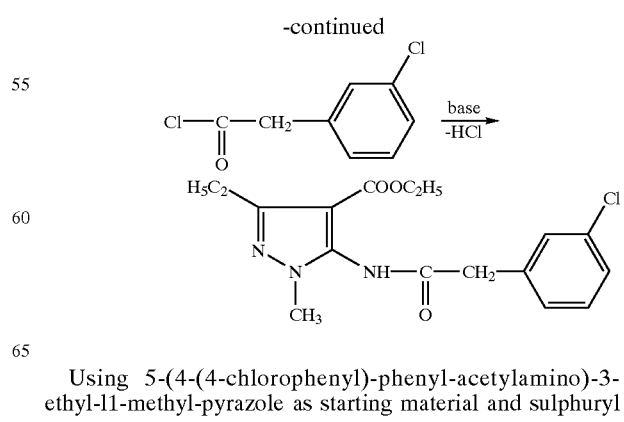

Using 5-(4-(4-chlorophenyl)-phenyl-acetylamino)-3-ethyl-l1-methyl-pyrazole as starting material and sulphuryl chloride as reaction component, the course of the process (b) according to the invention can be illustrated by the equation below.

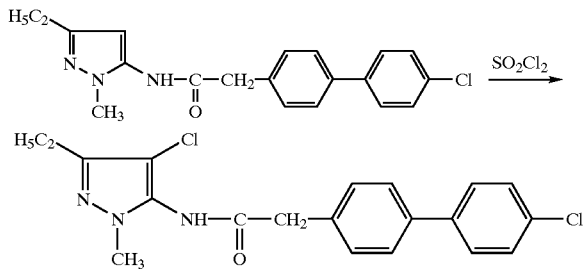

The 5-aminopyrazoles of the formula (II) and acyl halides of the formula (III) required as starting materials for carrying out the process (a) according to the invention are known or can be prepared by known methods (cf. WO-A 96-21 653).

Suitable acid binders for carrying out the process (a) according to the invention are all customary inorganic or organic bases. Preference is given to using alkali metal or alkaline earth metal hydroxides, carbonates or bicarbonates and also nitrogen bases. Examples which may be mentioned are sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

Suitable diluents for carrying out the process (a) according to the invention are all organic solvents which are customary for such reactions.

Preference is given to using optionally halogenated aliphatic or aromatic hydrocarbons, ethers or nitriles, such as, for example cyclohexane, toluene, chlorobenzene, chloroform, dichloromethane, dichloroethane, dioxane, tetrahydrofuran, diethyl ether or acetonitrile.

When carrying out the process (a) according to the invention, the reaction temperatures can be varied within a relatively wide range. In general, the process is carried out at temperatures between −40° C. and +150° C. preferably between 0° C. and 100° C.

The process (a) according to the invention is generally carried out under atmospheric pressure. However, it is also possible to operate under elevated or reduced pressure.

When carrying out the process (a) according to the invention, in general from 1 to 2 mol, preferably from 1 to 1.5 mol, of acyl halide of the formula (III) are employed per mole of 5-aminopyrazole of the formula (11). Work-up is carried out by customary methods.

The 5-amino-pyrazole derivatives of the formula (Ib) required as starting materials for carrying out the process (b) according to the invention are compounds which can be used according to the invention. They can be prepared by the process (a) according to the invention.

Suitable chlorinating agents for carrying out the process (b) according to the invention are all reagents which are customary for introducing chlorine. Preference is given to using chlorine gas, chlorine oxo acids and salts thereof, such as sodium hypochlorite or potassium hyprochlorite, furthermore chlorides, such as sulphuryl chloride, disulphur dichloride and phosphorus pentachloride.

Suitable diluents for carrying out the process (b) according to the invention are all organic solvents which are customary for such reactions.

Preference is given to using optionally halogenated aliphatic or aromatic hydrocarbons, ethers or nitriles, such as, for example, cyclohexane, toluene, chlorobenzene, chloroform, dichloromethane, dichloroethane, dioxane, tetrahydrofuran, diethyl ether or acetonitrile.

Suitable catalysts for carrying out the process (b) according to the invention are all reaction accelerators which are customary for such reactions. Preference is given to using hydrogen chloride, sodium acetate and free-radical formers, such as azoisobutyronitrile or dibenzoyl peroxide.

When carrying out the process (b) according to the invention, the reaction temperatures can likewise be varied within a relatively wide range. In general, the process is carried out at temperatures between −40° C. and +120° C., preferably between 0° C. and 80° C.

The process (b) according to the invention is generally carried out under atmospheric pressure. However, it is also possible to operate under elevated pressure.

When carrying out the process (b) according to the invention, in general from 1 to 2 mol, preferably from 1 to 1.5 mol, of chlorinating agent are employed per mole of 5-amino-pyrazole derivative of the formula (Ib). Work-up is again carried out by customary methods.

The compounds which can be used according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds which can be used according to the invention are particularly suitable for controlling Pyricularia oryzae on rice and for controlling cereal diseases, such as Puccinia, Erysiphe and Fusarium species. Moreover, the substances according to the invention can be used particularly successfully against Venturia, Podosphaera and Sphaerotheca. Moreover, they also have very good in vitro activity.

The active compounds which can be used according to the invention are also suitable for increasing the yield of crops. Moreover, they have reduced toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and rrricroencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use organic solvents, for example, auxiliary solvents. The following are mainly suitable as liquid solvents: aromatics such xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds which can be used according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:
- aldimorph, ampropylfos, ampropylfos potassium, andoprim, anilazine, azaconazole, azoxystrobin,
- benalaxyl, benodanil, benomyl, benzamacril, benzamacril-isobutyl, bialaphos, binapacryl, biphenyl, bitertanol, blasticidin-S, bromuconazole, bupirimate, buthiobate,
- calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
- edifenphos, epoxiconazole, etaconazole, ethirimol, etridiazole,
- famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalayl, furametpyr, furcarbonil, furconazole, furconazole-cis, furmecyclox, guazatine,
- hexachlorobenzene, hexaconazole, hymexazole,
- imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
- kasugamycin, kresoxim-methyl, copper preparations, such as: copper hydroxide, copper naphthenate, copper oxychloride, copper sulphate, copper oxide, oxine-copper and Bordeaux rnixture,
- mancopper, mancozeb, maneb, meferimzone, mepanipyrim, mepronil, metalaxyl, metconazole, methasulfocarb, methfuroxam, metiram, metomeclam, metsulfovax, imildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozen(PCNB), quinoxyfery
- sulphur and sulphur preparations,
- tebuconazole, tecloftalam, tecnazene, tetcyclasis, tetraconazole, thiabendazole, thicyofen, thifluzamide, thiophanate-methyl, thiram, tioxymnid, tolclofos-methyl, tolylfluanid, triadimefon, triadimenol, triazbutil, triazoxide, trichlamide, tricyclazole, tridemorph, triflumizole, triforine, triticonazole,
- uniconazole,
- validamycin A, vinclozolin, viniconazole,
- zarilarnide, zineb, ziram and also
- Dagger G,
- OK-8705,
- OK-8801,
- α-(1,1-dimethylethyl)-β-(2-phenoxyethyl)-1H- 1,2,4-triazole-1-ethanol,
- α-(2,4-dichlorophenyl)-β-fluoro-β-propyl-1H- 1,2,4-triazole- 1-ethanol,
- α-(2,4-dichlorophenyl)-β-methoxy-α-methyl-1H-1,2,4-triazole-1-ethanol,
- α-(5-methyl-1,3-dioxan-5-yl)-β[[4-(trifluoromethyl)-phenyl]-methylene]-1H-1,2, 4-triazole-1-ethanol,
- (5RS,6RS)-6-hydroxy-2,2,7,7-tetramethyl-5-(1H-1,2,4-triazol-1-yl)-3-octanone,
- (E)-α-(methoxyimino)-N-methyl-2-phenoxy-phenylacetamide,
- 1-isopropyl {2-methyl-1-[[[1-(4methylphenyl)-ethyl]-amino]-carbonyl]-propyl}-carbamate,
- 1-(2,4dichlorophenyl)-2-(1H-1,2,4-triazol-1-yl)-ethanone-O-(phenylmethyl)-oxime,
- 1-(2-methyl-1-naphthalenyl)-1H-pyrrole-2,5-dione,
- 1-(3,5-dichlorophenyl)-3-(2-propenyl)-2,5-pyrrolidinedione,
- 1-[(diiodomethyl)-sulphonyl]-4-methyl-benzene,
- 1-[[2-(2,4-dichlorophenyl)-1,3-dioxolan-2-yl]-methyl]-1H-imidazole,
- 1-[[2-(4-chlorophenyl)-3-phenyloxiranyl]-methyl]-1H-1, 2,4-triazole,
- 1-[1-[2-[(2,4-dichlorophenyl)-methoxy]-phenyl]-ethenyl]-1H-imidazole,
- 1-methyl-5-nonyl-2-(phenylmethyl)-3-pyrrolidinole,
- 2', 6'-dibromo-2-methyl4'-trifluoromethoxy-4'-trifluoro-methyl-1,3-thiazole-5-carboxanilide,
- 2,2-dichloro-N-[1-(4-chlorophenyl)-ethyl]-1-ethyl-3-methyl-cyclopropanecarboxamide,
- 2,6-dichloro-5-(methylthio)-4-pyrinidinyl-thiocyanate,
- 2,6-dichloro-N-(4-trifluoromethylbenzyl)-benzarnide,
- 2,6-dichloro-N-[[4-(trifluoromethyl)-phenyl]-methyl]-benzamide,
- 2-(2,3,3-triiodo-2-propenyl)-2H-tetrazole,
- 2-[(1-methylethyl)-sulphonyl]-5-(trichloromethyl)-1,3,4-thiadiazole, 2-[[6-deoxy4-O-(4-O-methyl-β-D-glycopyranosyl)-α-D-glucopyranosyl]-amino]-4-methoxy- 1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden4-yl)-3-pyridinecarboxamide, 2-chloro-N-(2,6-dimethylphenyl)-N-(isothiocyanatomethyl)-acetamide, 2-phenylphenol (OPP), 3,4dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4chlorophenyl)-azo]-cyanoacetate, potassium hydrogen carbonate, methanetetrathiol sodium salt, methyl 1-(2,3-dihydro-2,2-dimethyl- 1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamiide, N-[2,2,2-trichloro- 1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine 8 sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, Bactericides:
 bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
 abamectin, acephate, acrinathrin, alanycarb, aldicarb, alphamethrin, amitraz, avermectin, AZ 60541, azadirachtin, azinphos A, azinphos M, azocyclotin,
 Bacillus thuringiensis, 4bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
 cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cyprothrin, cyfluthrin, cyhalothrin, cyhexatin, cypermethrin, cyromazine,
 deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
 edifenphos, emamectin, esfenvalerate, ethiofencarb, ethion, ethofenprox, ethoprophos, etrimphos,
 fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
 HCH, heptenophos, hexaflumuron, hexythiazox,
 imidacloprid, iprobenfos, isazophos, isofenphos, isoprocarb, isoxathion, ivermectin, lambda-cyhalothrin, lufenuron,
 malathion, mecarbam, mervinphos, mesulfenphos, metaldehyde, methacrifos, methamidophos, methidathion, methiocarb, methomyl, metolcarb, milbemectin, monocrotophos, moxidectin,
 naled, NC 184, nitenpyram,
 omethoate, oxamyl, oxydemethon M, oxydeprofos,
 parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
 quinalphos,
 salithion, sebufos, silafluofen, sulfotep, sulprofos,
 tebufenozide, tebufenpyrad, tebupirimiphos, teflubenzuron, tefluthrin, temephos, terbam, terbufos, tetrachlorvinphos, thiafenox, thiamethoxam thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When employing the active compounds which can be used according to the invention as fungicides, the application rates can be varied within a relatively wide range, depending on the type of application. In the treatment of parts of plants, the active compound application rates are generally between 0.1 and 10,000 g/ha, preferably between 10 and 1000 g/ha. In the treatment of seed, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/ha.

The compositions used for the protection of industrial materials generally comprise an amount of 1 to 95% by weight, preferably 10 to 75% by weight, of the active compounds.

The use concentrations of the active compounds which can be used according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The activity and the activity spectrum of the active compounds to be used according to the invention in material protection, or of the compositions, concentrates or quite generally formulations preparable therefrom can be increased by adding, if appropriate, further antimicrobially achieve compounds, fungicides, bactericides, herbicides, insecticides or other active compounds for widening the activity spectrum or obtaining special effects, such as, for example, additional protection against insects. These mixtures may have a broader activity spectrum than the compounds according to the invention.

The preparation and the use of the active compounds according to the invention are illustrated by the examples below.

PREPARATION EXAMPLES

Example 1

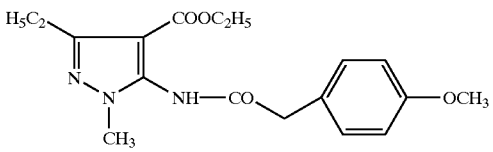

At room temperature, 0.47 g (0.006 mol) of pyridine is added to a solution of 0.99 g (0.005 mol) of 5-amino-4-ethoxycarbonyl-3-ethyl-1-methylpyrazole in 80 ml of dichloromethane. At the same temperature, a solution of 1.11 g (0.006 mol) of 4-methoxyphenylacetyl chloride in 20 ml of dichloromethane is then added dropwise. The mixture is stirred overnight at room temperature and then under reflux for 24 hours. After cooling, the reaction mixture is washed with dilute HCl and with dilute aqueous $NaHCO_3$ solution. The organic phase is dried over $MgSO_4$, filtered and evaporated to dryness.

This gives 1.28 g (74% of theory) of 4-ethoxycarbonyl-3-ethyl-5-(4-methoxyphenylacetyl)-amino-1-methylpyrazole as a yellowish solid of melting point 112 to 113° C.

Example 2

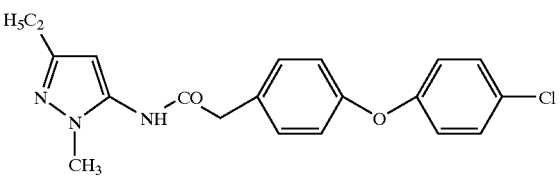

At room temperature, 0.95 g (0.012 mol) of pyridine is added to a solution of 1.25 g (0.01 mol) of 5-amino-3-ethyl-1-methylpyrazole in 120 ml of dichloromethane. At the same temperature, a solution of 3.37 g (0.012 mol) of 4-(4-chlorophenoxy)phenylacetyl chloride in 30 ml of dichloromethane is then added dropwise. The mixture is stirred overnight at room temperature and then washed successively with dilute HCl and dilute aqueous $NaHCO_3$ solution, dried over $MgSO_4$, filtered and evaporated to dryness.

This gives 3.10 g (84% of theory) of 5-(4-(4-chlorophenoxy)-phenylacetylamino)-3-ethyl-1-methylpyrazole as a brown oil.

$^1$H-NMR ($CDCl_3$): =1.19, 2.57, 3.56, 3.63, 3.73, 6.04, 6.92–7.03, 7.27–7.33 ppm Example 3

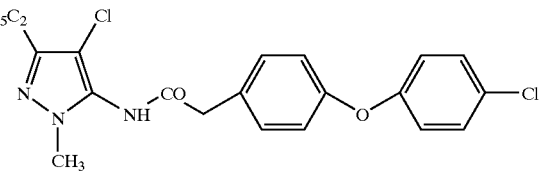

At 0° C., 0.37 g (0.00275 mol) of sulphuryl chloride is added dropwise to a solution of 0.92 g (0.0025 mol) of 5-(4-(4-chlorophenoxy)phenylacetylamino)-3-ethyl-1-methylpyrazole (Ex. 2) in 10 ml of dichloromethane. The mixture is stirred overnight at room temperature and then diluted with 10 ml of dichloromethane and washed successively with water, saturated aqueous NaHCO₃ solution and saturated aqueous NaCl solution, dried over MgSO₄, filtered and evaporated to dryness.

This gives 0.80 g (79% of theory) of 4-chloro-5-(4-(4-chlorophenoxy)-phenylacetylamino)-3-ethyl-1-methylpyrazole as a brown oil.

¹H-NMR (CDCl₃): =1.21, 2.57, 3.63, 3.77, 6.82, 6.92–7.04, 7.30–7.35 ppm

Example 4

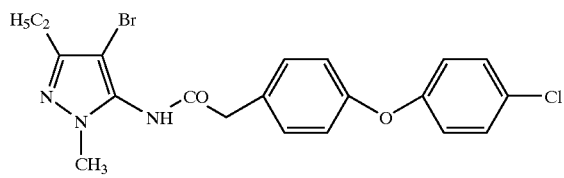

At 0° C., 0.44 g (0.00275 mol) of bromine is added dropwise to a solution of 0.92 g (0.0025 mol) of 5-(4-(4-chlorophenoxy)phenylacetylamino)-3-ethyl-1-methylpyrazole (Ex. 2) in 10 ml of dichloromethane. The mixture is stirred overnight at room temperature and then diluted with 10 ml of dichloromethane and washed successively with water, saturated aqueous NaHCO₃ solution and saturated aqueous NaCl solution, dried over MgSO₄, filtered and evaporated to dryness.

This gives 0.90 g (80% of theory) of 4-bromo-5-(4-(4-chlorophenoxy)-phenylacetylamino)-3-ethyl-1-methylpyrazole as a brown oil.

¹H-NMR (CDCl₃): =1.20, 2.56, 3.66, 3.77, 6.80, 6.91–7.04, 7.27–7.36 ppm

Example 5

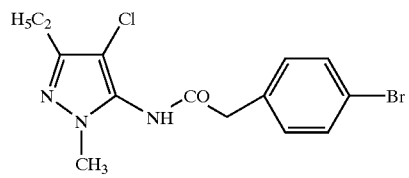

At room temperature, 1.90 g (0.024 mol) of pyridine are added to a solution of 3.19 g (0.02 mol) of 5-amino4-chloro-3-ethyl-1-methylpyra?ole (Ex. IV-1) in 120 ml of dichloromethane. At the same temperature, a solution of 5.60 g (0.024 mol) of 4-bromophenylacetyl chloride in 30 ml of dichloromethane is then added dropwise. The mixture is stirred overnight at room temperature and then washed with dilute HCl and dilute aqueous NaHCO₃ solution. The organic phase is dried over MgSO₄, filtered and evaporated to dryness.

This gives 4.61 g (63% of theory) of 5-(4-bromophenylacetyl)-amino-4-chloro-3-ethyl-1-methylpyrazole as a colourless solid of melting point 167–168° C.

The 5-amino-pyrazole derivatives of the formula (I) listed in Table 2 below are likewise prepared by the methods mentioned above.

TABLE 2

(I)

| Ex. No. | R¹ | R² | R³ | R⁴ | —Y—R⁵ | Melting point or δ value (ppm; ¹H—NMR in CDCl₃) |
|---|---|---|---|---|---|---|
| 6 | CH₃ | CN | CH₃ | H | —CH₂—C₆H₄—t-C₄H₉ | 1.27; 2.22; 3.34; 3.57 *) |
| 7 | C₂H₅ | CN | CH₃ | H | —CH₂—C₆H₄—t-C₄H₉ | 124–127° C. |
| 8 | C₂H₅ | CN | CH₃ | H | —CH₂—C₆H₄—OCH₃ | 127–128° C. |
| 9 | C₂H₅ | CN | CH₃ | H | —CH₂—C₆H₄—Cl | 148–151° C. |
| 10 | C₂H₅ | CN | CH₃ | H | —CH₂—C₆H₄—Br | 153–154° C. |

TABLE 2-continued

Structure (I): pyrazole with R¹ at 3-position, R² at 4-position, R³ on N1, and at 5-position N(R⁴)–C(=O)–Y–R⁵

| Ex. No. | R¹ | R² | R³ | R⁴ | —Y—R⁵ | Melting point or δ value (ppm; ¹H—NMR in CDCl₃) |
|---|---|---|---|---|---|---|
| 11 | C₂H₅ | CN | CH₃ | H | —CH₂—(3,4-dichlorophenyl) | 171–173° C. |
| 12 | C₂H₅ | CN | CH₃ | H | —CH₂—(4-(4-OCF₃-phenyl)phenyl) | 152–155° C. |
| 13 | C₂H₅ | CN | CH₃ | H | —CH₂—C₆H₄—O—C₆H₄—Cl | 126–128° C. |
| 14 | C₂H₅ | CN | CH₃ | H | —CH₂—C₆H₄—O—C₆H₄—OCF₃ | 1.27; 1.68; 3.62; 3.77 |
| 15 | C₂H₅ | CN | CH₃ | H | —CH₂—C₆H₄—O—C₆H₄—CN | 170–171° C. |
| 16 | C₂H₅ | CN | CH₃ | H | —CH₂—C₆H₄—O—C₆H₄—NO₂ | 169–172° C. |
| 17 | C₂H₅ | H | CH₃ | H | —CH₂—C₆H₄—O—C₆H₄—OCF₃ | 1.19; 2.57; 3.73; 6.04 |
| 18 | C₂H₅ | H | CH₃ | H | —CH₂—C₆H₄—O—C₆H₄—Cl | 1.13; 1.26; 2.64; 3.37; 3.42; 5.91; |
| 19 | C₂H₅ | Cl | CH₃ | H | —CH₂—C₆H₄—O—C₆H₄—OCF₃ | 101–103° C. |
| 20 | C₂H₅ | Cl | CH₃ | C₂H₅ | —CH₂—C₆H₄—O—C₆H₄—Cl | 1.14; 1.28; 2.66 |
| 21 | C₂H₅ | Br | CH₃ | H | —CH₂—C₆H₄—O—C₆H₄—OCF₃ | 111–112° C. |
| 22 | C₂H₅ | Br | CH₃ | C₂H₅ | —CH₂—C₆H₄—O—C₆H₄—Cl | 1.15; 1.28; 3.29 |

TABLE 2-continued (I) Structure: pyrazole with R¹ at 3-position, R² at 4-position, N-R³ at 1-position, and at 5-position: N(R⁴)-C(=O)-Y-R⁵

| Ex. No. | R¹ | R² | R³ | R⁴ | —Y—R⁵ | Melting point or δ value (ppm; ¹H—NMR in CDCl₃) |
|---|---|---|---|---|---|---|
| 23 | C₂H₅ | NO₂ | CH₃ | H | —CH₂—C₆H₄—O—C₆H₄—OCF₃ | 1.24; 2.89; 3.76; 3.83; 8.48 |
| 24 | C₂H₅ | COOC₂H₅ | CH₃ | H | —CH₂—C₆H₄—t-C₄H₉ | 1.20; 1.28; 1.32; 2.78; 3.69; 3.75; 4.20 |
| 25 | C₂H₅ | COOC₂H₅ | CH₃ | H | —CH₂—C₆H₄—Cl | 133–135° C. |
| 26 | C₂H₅ | COOC₂H₅ | CH₃ | H | —CH₂—C₆H₄—Br | 1.21; 1.32; 2.76; 3.68; 3.73; 4.25; 8.44 |
| 27 | C₂H₅ | COOC₂H₅ | CH₃ | H | —CH₂—C₆H₃(Cl)(Cl) | 156–158° C. |
| 28 | C₂H₅ | COOC₂H₅ | CH₃ | H | —CH₂—C₆H₄—C₆H₄—OCF₃ | 1.22; 1.35; 2.74; 3.56; 4.28; 5.04 |
| 29 | C₂H₅ | COOC₂H₅ | CH₃ | H | —CH₂—C₆H₄—O—C₆H₄—Cl | 1.21; 1.32; 2.78; 3.70; 3.76; 4.25 |
| 30 | C₂H₅ | COOC₂H₅ | CH₃ | H | —CH₂—C₆H₄—O—C₆H₄—OCF₃ | 1.21; 1.32; 2.78; 3.71; 3.77; 4.25; 8.48 |
| 31 | C₂H₅ | COOC₂H₅ | CH₃ | H | —CH₂—C₆H₄—O—C₆H₄—CN | 145–147° C. |
| 32 | C₂H₅ | COOC₂H₅ | CH₃ | H | —CH₂—C₆H₄—O—C₆H₄—NO₂ | 114–117° C. |
| 33 | C₂H₅ | Cl | CH₃ | H | —CH₂—C₆H₄—O—C₆H₄—NO₂ | 150–151° C. |
| 34 | C₂H₅ | Cl | CH₃ | H | —CH₂—C₆H₄—O—C₆H₄—CN | 147° C. |

TABLE 2-continued

Structure (I):

Pyrazole with R¹ at 3-position, R² at 4-position, R³ on N1, and at 5-position: N(R⁴)—C(=O)—Y—R⁵

| Ex. No. | R¹ | R² | R³ | R⁴ | —Y—R⁵ | Melting point or δ value (ppm; ¹H—NMR in CDCl₃) |
|---|---|---|---|---|---|---|
| 35 | C₂H₅ | Cl | CH₃ | H | —CH₂—(C₆H₄)—(C₆H₄)—OCF₃ | 147° C. |
| 36 | C₂H₅ | H | CH₃ | H | —CH₂—(C₆H₄)—O—(C₆H₄)—CN | 1.20; 2.56; 3.58; 3.76; 6.05 |
| 37 | C₂H₅ | —COOCH₃ | CH₃ | H | —CH₂—(C₆H₄)—O—(C₆H₄)—CN | 162° C. |
| 38 | C₂H₅ | —COOCH₃ | CH₃ | H | —CH₂—(C₆H₄)—O—(C₆H₄)—NO₂ | 1.21; 2.71; 3.73; 3.78; 3.82 |
| 39 | C₂H₅ | —COOCH₃ | CH₃ | H | —CH₂—(C₆H₄)—O—(C₆H₄)—OCF₃ | 1.20; 2.79; 3.71; 3.76; 3.78 |
| 40 | C₂H₅ | Br | CH₃ | H | —CH₂—(C₆H₄)—O—(C₆H₄)—CN | 134° C. |
| 41 | C₂H₅ | COOC₂H₅ | CH₃ | CH₃ | —CH₂—(C₆H₄)—O—(C₆H₄)—CN | 1.29; 2.90; 3.15; 3.41; 3.43; 4.22 |
| 42 | C₂H₅ | COOC₂H₅ | CH₃ | CH₃ | —CH₂—(C₆H₄)—O—(C₆H₄)—NO₂ | 1.29; 2.74; 3.16; 3.44; 3.45; 4.22 |
| 43 | C₂H₅ | COOC₂H₅ | CH₃ | CH | —CH₂—(C₆H₄)—O—(C₆H₄)—Cl | 1.28; 2.90; 3.13; 3.34; 3.41; 4.20 |
| 44 | C₂H₅ | COOC₂H₅ | CH₃ | H | —CH₂—(C₆H₄)—O—(C₆H₄)—C₄H₉-t | 1.32; 2.77; 3.70; 3.75; 4.23 |
| 45 | C₂H₅ | CN | CH₃ | H | —CH₂—(C₆H₄)—O—(C₆H₄)—C₄H₉-t | 1.31; 2.67; 3.61; 3.76 |
| 46 | C₂H₅ | —COOC₂H₅ | CH₃ | H | —CH₂—(m-C₆H₄)—O—(C₆H₄)—NO₂ | 1.21; 1.33; 2.76; 3.71; 3.80; 4.22 |

TABLE 2-continued
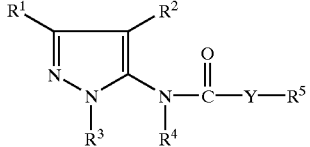
(I)
| Ex. No. | R¹ | R² | R³ | R⁴ | —Y—R⁵ | Melting point or δ value (ppm; ¹H—NMR in CDCl₃) |
|---|---|---|---|---|---|---|
| 47 | $C_2H_5$ | CN | $CH_3$ | H | 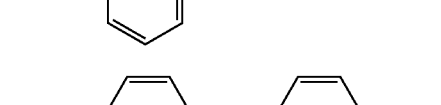 | 62–64° C. |
| 48 | $C_2H_5$ | —COOC₂H₅ | $CH_3$ | H | 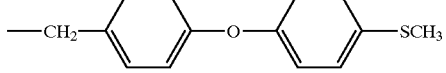 | 1.20; 1.30; 2.48; 2.76; 3.70; 3.75; 4.23 |
| 49 | $C_2H_5$ | CN | $CH_3$ | H | 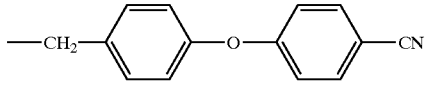 | 53–54° C. |
| 50 | $CH_3$ | CN | $CH_3$ | H | 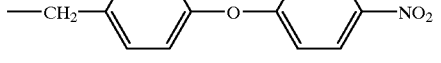 | 101° C. |
| 51 | $CH_3$ | CN | $CH_3$ | H |  | 102–104° C. |
| 52 | $CH_3$ | CN | $CH_3$ | H |  | 135–138° C. |
| 53 | $CH_3$ | —COOC₂H₅ | $CH_3$ | H |  | 141–142° C. |
| 54 | $CH_3$ | —COOC₂H₅ | $CH_3$ | H | 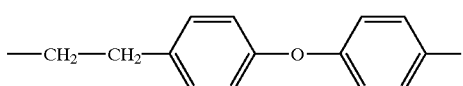 | 142–144° C. |
| 55 | $CH_3$ | —COOC₂H₅ | $CH_3$ | H | 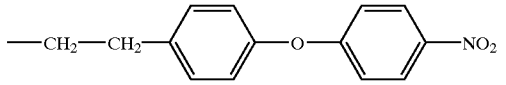 | 1.32; 2.36; 3.70; 3.76; 4.25 |
| 56 | $C_2H_5$ | —COOC₂H₅ | $CH_3$ | H | 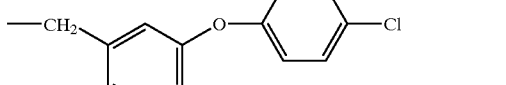 | 1.22; 1.36; 2.80; 3.70; 4.29 |
| 57 | $C_2H_5$ | CN | $CH_3$ | H |  | 62–64° C. |
| 58 | $C_2H_5$ | —COOC₂H₅ | $CH_3$ | H |  | 1.21; 1.29; 2.76; 3.69; 3.75 |

TABLE 2-continued
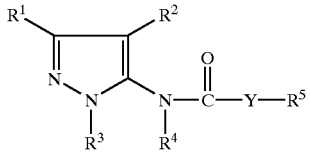
(I)
| Ex. No. | R¹ | R² | R³ | R⁴ | —Y—R⁵ | Melting point or δ value (ppm; ¹H—NMR in CDCl₃) |
|---|---|---|---|---|---|---|
| 59 | $C_2H_5$ | CN | $CH_3$ | H | 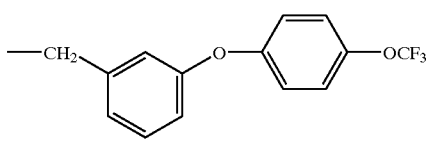 | 58–60° C. |
| 60 | $C_2H_5$ | —$COOC_2H_5$ | $CH_3$ | H | 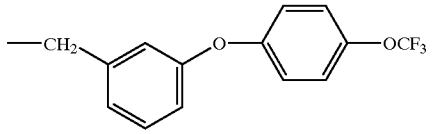 | 81° C. |
| 61 | $C_2H_5$ | CN | $CH_3$ | H | 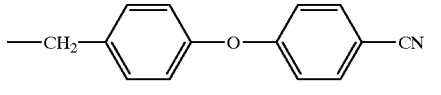 | 133° C. |
| 62 | $C_2H_5$ | $COOC_3H_7$-i | $CH_3$ | H | 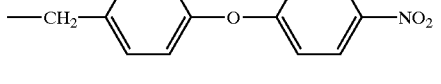 | 126–128° C. |
| 63 | $C_2H_5$ | $COOC_3H_7$-i | $CH_3$ | H | 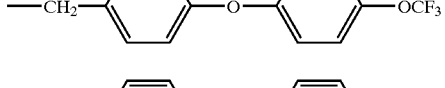 | 82° C. |
| 64 | $C_2H_5$ | $COOC_3H_7$-i | $CH_3$ | H |  | 75° C. |
| 65 | $C_2H_5$ | CN | $C_4H_9$-t | H | 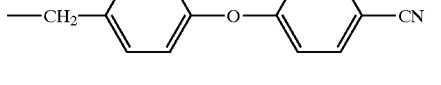 | 165–167° C. |
| 66 | $C_2H_5$ | —$COOC_2H_5$ | $CH_3$ | H | 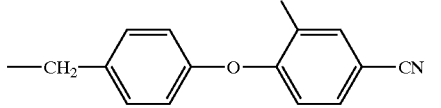 | 126–128° C. |
| 67 | $C_2H_5$ | CN | $CH_3$ | H | 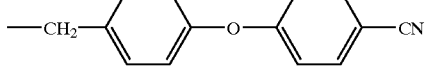 | 105–107° C. |
| 68 | $C_2H_5$ | —$COOC_2H_5$ | $C_4H_9$-t | H |  | 184° C. |

TABLE 2-continued
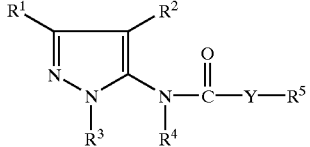
(I)
| Ex. No. | R¹ | R² | R³ | R⁴ | —Y—R⁵ | Melting point or δ value (ppm; ¹H—NMR in CDCl₃) |
|---|---|---|---|---|---|---|
| 69 | $C_2H_5$ | —$COOC_2H_5$ | $C_4H_9$-t | H | 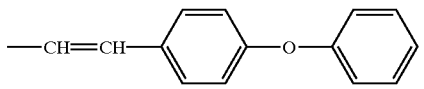 | 171° C. |
| 70 | $C_2H_5$ | —$COOC_2H_5$ | $CH_3$ | H | 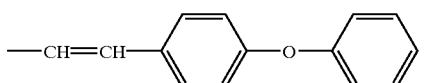 | 120° C. |
| 71 | $C_2H_5$ | CN | $CH_3$ | H | 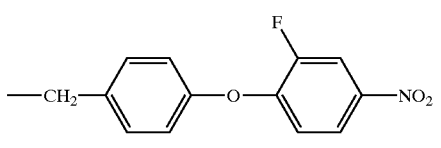 | 178° C. |
| 72 | $C_2H_5$ | —$COOC_2H_5$ | $CH_3$ | H | 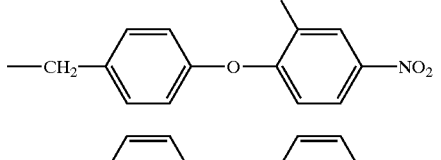 | 131° C. |
| 73 | $C_2H_5$ | CN | $CH_3$ | H |  | 163° C. |
| 74 | $C_2H_5$ | —$COOCH_2$—$CH$=$CH_2$ | $CH_3$ | H |  | 121° C. |
| 75 | $C_2H_5$ | —$COOCH_2$—$CH$=$CH_2$ | $CH_3$ | H |  | 1.22; 2.79; 3.73; 3.81 |
| 76 | $C_2H_5$ | —$COOC_2H_5$ | $C_3H_7$-i | H |  | 125–127° C. |
| 77 | $C_2H_5$ | —$COOC_2H_5$ | $C_3H_7$-i | H |  | 124° C. |
| 78 | $C_2H_5$ | CN | $C_3H_7$-i | H |  | 168° C. |
| 79 | $C_2H_5$ | CN | $C_3H_7$-i | H |  | 190–192° C. |
| 80 | $C_4H_9$-t | H | $CH_3$ | H |  | 70–71° C. |

TABLE 2-continued (I)

| Ex. No. | R¹ | R² | R³ | R⁴ | —Y—R⁵ | Melting point or δ value (ppm; ¹H—NMR in CDCl₃) |
|---|---|---|---|---|---|---|
| 81 | $C_2H_5$ | —COOC$_2$H$_5$ | CH$_3$ | H | —CH$_2$—C$_6$H$_3$(F)$_2$—O—C$_6$H$_3$(F)—CN | 186–187° C. |
| 82 | $C_2H_5$ | CN | CH$_3$ | H | —CH$_2$—C$_6$H$_4$—O—C$_6$H$_2$(F)$_2$—CN | 168° C. |
| 83 | $C_4H_9$-t | Br | CH$_3$ | H | —CH$_2$—C$_6$H$_4$—O—C$_6$H$_4$—CN | 95° C. |
| 84 | $C_4H_9$-t | Cl | CH$_3$ | H | —CH$_2$—C$_6$H$_4$—O—C$_6$H$_4$—CN | 1.34; 3.65; 3.81 |
| 85 | $C_2H_5$ | —COOC$_2$H$_5$ | CH$_3$ | H | —CH$_2$O—C$_6$H$_4$—O—C$_6$H$_4$—CN | 85° C. |
| 86 | $C_2H_5$ | CN | CH$_3$ | H | —CH$_2$O—C$_6$H$_4$—O—C$_6$H$_4$—CN | 110–111° C. |
| 87 | $C_2H_5$ | —COOC$_2$H$_5$ | CH$_3$ | H | —CH$_2$—C$_6$H$_4$—O—C$_6$H$_4$—SCF$_3$ | 1.21; 1.33; 2.79; 3.72; 3.79 |
| 88 | $C_2H_5$ | CN | CH$_3$ | H | —CH$_2$—C$_6$H$_4$—O—C$_6$H$_4$—SCF$_3$ | 1.25; 2.67; 3.63; 3.79 |

*) ¹H—NMR in DMSO-d₆

Example 89

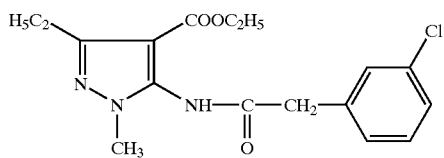

A mixture of 1.0 g (4.70 mmol) of 5-amino-3-ethyl-4-ethoxycarbonyl-1-methyl-pyrazole, 0.75 g (9.40 mmol) of pyridine and 10 ml of methylene chloride is mixed with 1.07 g (5.60 mmol) of (3-chlorophenyl)-acetyl chloride and stirred at 20° C. for 18 hours. The reaction mixture is then admixed with methylene chloride and water. The organic phase is separated off, washed successively with 10% strength aqueous hydrochloric acid and saturated aqueous-sodium bicarbonate solution, and then dried over magnesium sulphate, filtered and concentrated under reduced pressure. This gives 0.97 g (59% of theory) of 5-(3-chloro-phenyl-acetyl)-amino-3-ethyl4-ethoxycarbonyl-1-methyl-pyrazole in the form of an oily liquid. log P (acidic): 2.65

The 5-amino-pyrazole derivatives of the formula (I) listed in Table 3 below are likewise prepared by the methods mentioned above.

TABLE 3

(I)

| Ex No. | $R^1$ | $R^2$ | $R^3$ | $R^4$ | —Y—$R^5$ | Melting point or log P value |
|---|---|---|---|---|---|---|
| 90 | $C_2H_5$ | Cl | $CH_3$ | H | —$CH_2$—C6H4—C6H4—Cl | 164° C. |
| 91 | $C_2H_5$ | Cl | $CH_3$ | H | —$CH_2$—C6H4—C6H4—$OCH_3$ | 187° C. |
| 92 | $C_2H_5$ | H | $CH_3$ | H | —$CH_2$—C6H4—C6H4—$OCF_3$ | 147° C. |
| 93 | $C_2H_5$ | $COOC_2H_5$ | $CH_3$ | H | —$CH_2$—C6H4—Br | 135° C. |
| 94 | $C_2H_5$ | CN | $CH_3$ | H | —$CH_2$—C6H4—Br | 167° C. |
| 95 | $C_2H_5$ | $COOC_2H_5$ | $CH_3$ | H | —$CH_2$—C6H4—$OCH_3$ | log P = 2.28 |
| 96 | $C_2H_5$ | $COOC_2H_5$ | $CH_3$ | H | —$CH_2$—C6H4—$OCH_3$ | log P = 2.88 |

Preparation of the Compound of Example 35

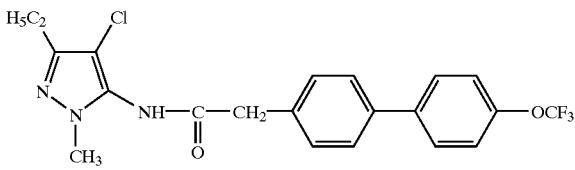

At room temperature, 26.74 g (75 mmol) of 5-(4-bromophenylacetyl)-amino-4-chloro-3-ethyl-1-methyl-pyrazole and 117 ml of 2 molar aqueous sodium carbonate solution are added dropwise to a mixture of 5.25 g (4.5 mmol) of tetrakis-(triphenylphosphonine)-palladium and 150 ml of toluene with stirring. With vigorous stirring, a solution of 20.48 g (82.5 mmol) of 4-trifluoromethoxyphenyl-boronic acid in 75 ml of ethanol is then added dropwise at room temperature. The reaction mixture is initially heated under reflux for 16 hours and then cooled to room temperature and admixed with water and diethyl ether. The organic phase is separated off, washed with aqueous sodium chloride solution, dried over magnesium sulphate, filtered and concentrated under reduced pressure. The product that remains is chromatographed over silica gel using a mixture of methylene chloride/ethyl acetate =1:1. This gives 16.94 g (52% of theory) of the compound of the formula given above, in the form of a solid of melting point 174° C.

The 5-amino-pyrazole derivatives of the formula

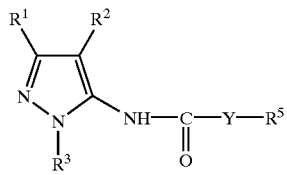

(Ic)

listed in Table 4 below are likewise prepared by the methods given above.

TABLE 4

| Ex. No. | $R^1$ | $R^2$ | $R^3$ | —Y—$R^5$ | Physical constant |
|---|---|---|---|---|---|
| 97 | —CH$_3$ | H | —CH$_3$ | —CH$_2$—⟨C$_6$H$_4$⟩—C(CH$_3$)$_3$ | |
| 98 | —CH$_3$ | H | —CH$_3$ | —CH$_2$—O—⟨2,3-(CH$_3$)$_2$C$_6$H$_3$⟩ | |
| 99 | —CH$_3$ | Br | —CH$_3$ | —CH$_2$—O—⟨2,3-(CH$_3$)$_2$-4-Br-C$_6$H$_2$⟩ | |
| 100 | —CH$_3$ | Cl | —CH$_3$ | —CH$_2$—⟨C$_6$H$_4$⟩—C$_4$H$_9$-t | |
| 101 | C$_2$H$_5$ | —CN | —CH$_3$ | —CH$_2$—(2,3-dihydrobenzofuran-5-yl) | mp = 158–159° C. |
| 102 | C$_2$H$_5$ | Cl | —CH$_3$ | —CH$_2$—(2,4,6-trimethylphenyl) | logP = 3.01 |
| 103 | C$_2$H$_5$ | —CN | —CH$_3$ | —CH$_2$—⟨C$_6$H$_4$⟩—O—(3-Cl-5-CF$_3$-pyridin-2-yl) | mp = 178–179° C. |

TABLE 4-continued
| Ex. No. | R¹ | R² | R³ | —Y—R⁵ | Physical constant |
|---|---|---|---|---|---|
| 104 | C₂H₅ | —COOC₂H₅ | —CH₃ | 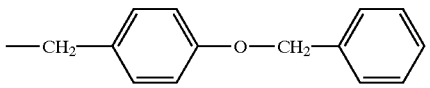 | logP = 3.26 |
| 105 | C₂H₅ | H | —CH₃ | 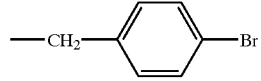 | logP = 2.13 |
| 106 | C₂H₅ | —COOC₂H₅ | —CH₃ | 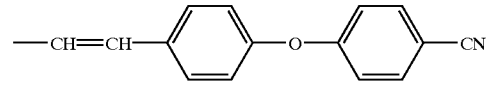 | logP = 3.16 |
| 107 | C₂H₅ | —COOC₂H₅ | —CH₃ | 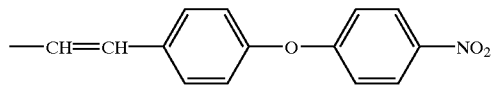 | logP = 3.41 |
| 108 | C₂H₅ | —CN | —CH₃ | 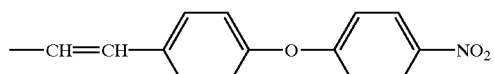 | logP = 3.05 |
| 109 | cyclopropyl | H | CH₃ | 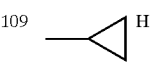 | logP = 2.45 |
| 110 | cyclopropyl | Cl | CH₃ | 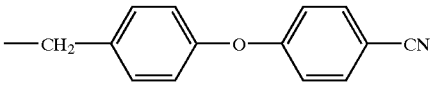 | logP = 2.90 |
| 111 | C₂H₅ | —COOC₂H₅ | —CH₃ | 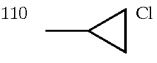 | logP = 3.28 |
| 112 | —CH₃ | Cl | —CH₃ | 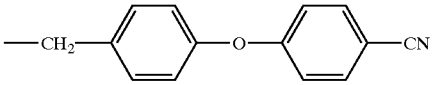 | mp = 125–128° C. |
| 113 | —CH₃ | H | —CH₂—CH₂—CN | 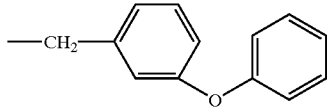 | logP = 1.77 |
| 114 | —CH₃ | —CN | —CH₃ | 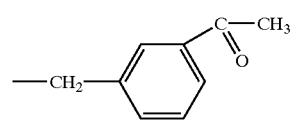 | logP = 1.48 |
| 115 | C₂H₅ | —CN | —CH₃ | 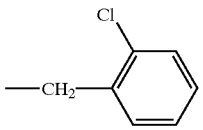 | logP = 1.71 |
| 116 | —CH₃ | —COO—CH₃ | —CH₃ | 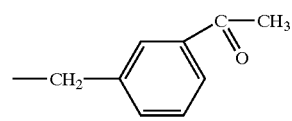 | logP = 1.50 |

TABLE 4-continued
| Ex. No. | R¹ | R² | R³ | —Y—R⁵ | Physical constant |
|---|---|---|---|---|---|
| 117 | —CH₃ | Cl | —CH₃ | 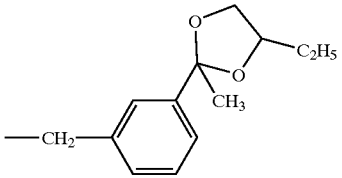 | |
| 118 | —CH₃ | Cl | —CH₃ | 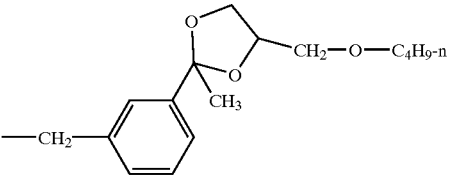 | |
| 119 | —CH₃ | —CN | —CH₃ | 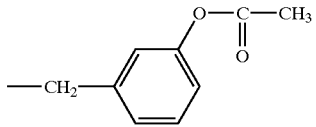 | logP = 1.88 |
| 120 | C₂H₅ | —CN | —CH₃ | 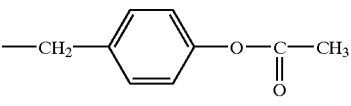 | logP = 1.84 |
| 121 | —CH₃ | H | —CH₃ | 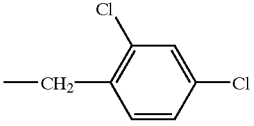 | logP = 2.06 |
| 122 | —CH₃ | Cl | —CH₃ | 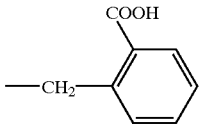 | logP = 1.50 |
| 123 | —CH₃ | Cl | —CH₃ | 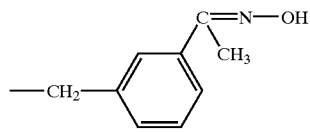 | logP = 1.85 |
| 124 | —CH₃ | Cl | —CH₃ | 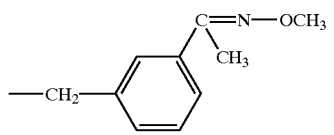 | logP = 2.32 |
| 125 | —CH₃ | Cl | —CH₃ | 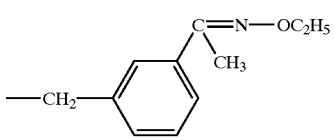 | logP = 2.88 |
| 126 | —CH₃ | Cl | —CH₃ | 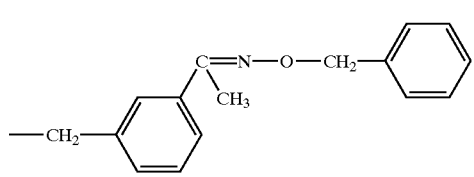 | logP = 3.31 |

TABLE 4-continued

| Ex. No. | R¹ | R² | R³ | —Y—R⁵ | Physical constant |
|---|---|---|---|---|---|
| 127 | —CH$_3$ | Cl | —CH$_3$ | —CH$_2$—(3-substituted phenyl)—C(CH$_3$)=N—O—CH$_2$—(4-CF$_3$-phenyl) | logP = 3.83 |
| 128 | —CH$_3$ | Cl | —CH$_3$ | —CH$_2$—(3-substituted phenyl)—C(CH$_3$)=N—O—CH$_2$—(6-chloropyridin-3-yl) | logP = 2.80 |
| 129 | —CH$_3$ | Cl | —CH$_3$ | —CH$_2$—(3-substituted phenyl)—C(CH$_3$)=N—O—CH$_2$—(2,4-dichlorophenyl) | logP = 4.30 |
| 130 | —CH$_3$ | Cl | —CH$_3$ | —CH$_2$—(3-substituted phenyl)—C(CH$_3$)=N—O—C(CH$_3$)$_3$ | logP = 3.53 |
| 131 | —CH$_3$ | Cl | —CH$_3$ | —CH$_2$—(3-substituted phenyl)—C(CH$_3$)=N—O—CH$_2$—(2,6-dichlorophenyl) | logP = 3.91 |
| 132 | —CH$_3$ | Cl | —CH$_3$ | —CH$_2$—(3-substituted phenyl)—C(CH$_3$)=N—O—CH$_2$—CH=CH$_2$ | logP = 2.80 |
| 133 | —CH$_3$ | Cl | —CH$_3$ | —CH$_2$—(2-substituted phenyl)—C(=O)—NH—C$_3$H$_{7}$-n | logP = 1.92 |
| 134 | —CH$_3$ | Cl | —CH$_3$ | —CH$_2$—(2-substituted phenyl)—C(=O)—NH—CH$_2$—(6-chloropyridin-3-yl) | logP = 1.91 |
| 135 | —CH$_3$ | —COO—CH$_3$ | —CH$_3$ | —CH$_2$—(3-bromophenyl) | logP = 2.11 |

TABLE 4-continued
| Ex. No. | R¹ | R² | R³ | —Y—R⁵ | Physical constant |
|---|---|---|---|---|---|
| 136 | C₂H₅ | —CN | —CH₃ | 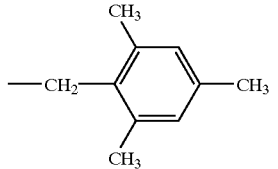 | logP = 2.83 |
| 137 | —CH₃ | —CN | —CH₃ | 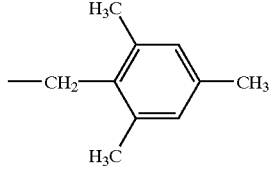 | logP = 2.36 |
| 138 | —CH₃ | Cl | —CH₃ | 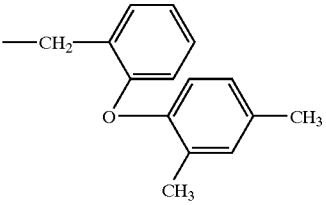 | logP = 3.44 |
| 139 | —CH₃ | Cl | —CH₃ | 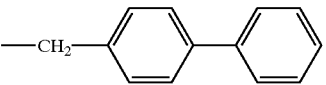 | logP = 2.81 |
| 140 | —CH₃ | Cl | —CH₃ | 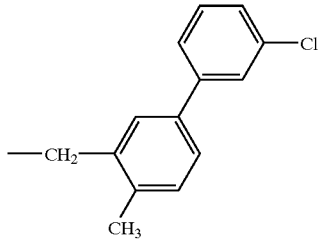 | logP = 3.53 |
| 141 | —CH₃ | Cl | —CH₃ | 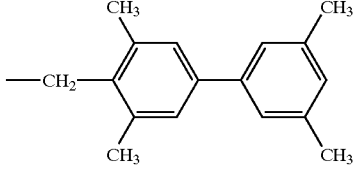 | logP = 4.09 |
| 142 | —CH₃ | Cl | —CH₃ | 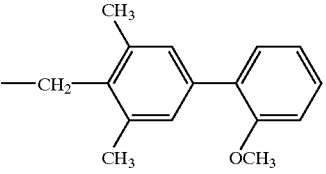 | logP = 3.25 |
| 143 | —CH₃ | Cl | —CH₃ | 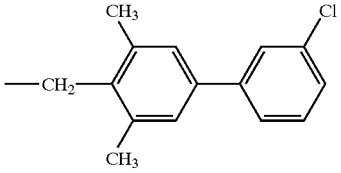 | logP = 3.79 |

TABLE 4-continued
| Ex. No. | R¹ | R² | R³ | —Y—R⁵ | Physical constant |
|---|---|---|---|---|---|
| 144 | —CH₃ | Cl | —CH₃ | 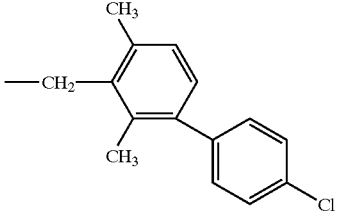 | logP = 3.84 |
| 145 | —CH₃ | Cl | —CH₃ | 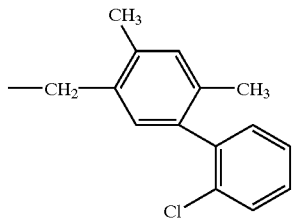 | logP = 3.64 |
| 146 | —CH₃ | Cl | —CH₃ | 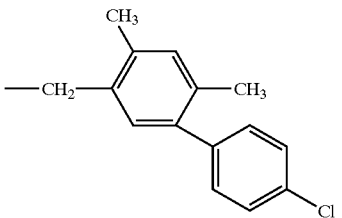 | logP = 3.82 |
| 147 | —CH₃ | Cl | —CH₃ | 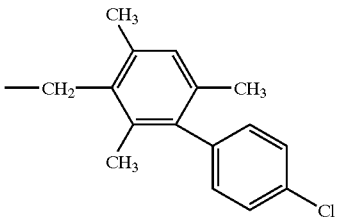 | logP = 4.08 |
| 148 | —CH₃ | Cl | —CH₃ | 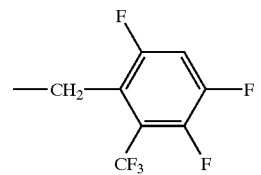 | logP = 2.60 |
| 149 | —CH₃ | —CN | —CH₃ | 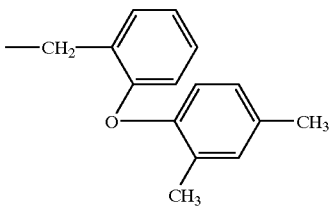 | logP = 3.17 |
| 150 | —CH₃ | —CN | —CH₃ | 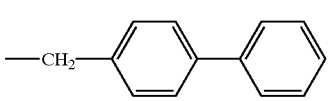 | logP = 2.57 |

TABLE 4-continued
| Ex. No. | R¹ | R² | R³ | —Y—R⁵ | Physical constant |
|---|---|---|---|---|---|
| 151 | —CH₃ | —CN | —CH₃ | 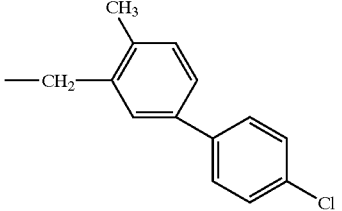 | logP = 3.20 |
| 152 | —CH₃ | —CN | —CH₃ | 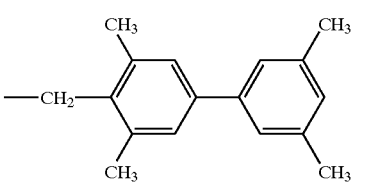 | logP = 3.88 |
| 153 | —CH₃ | —CN | —CH₃ | 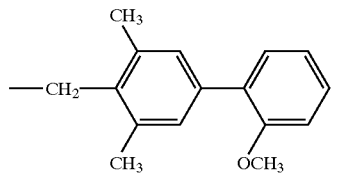 | logP = 2.95 |
| 154 | —CH₃ | —CN | —CH₃ | 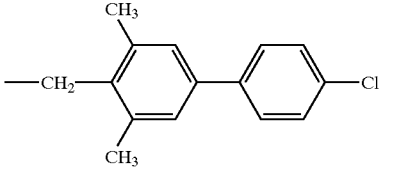 | logP = 3.46 |
| 155 | —CH₃ | —CN | —CH₃ | 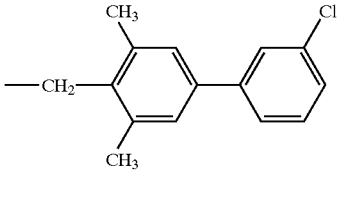 | logP = 3.42 |
| 156 | —CH₃ | —CN | —CH₃ | 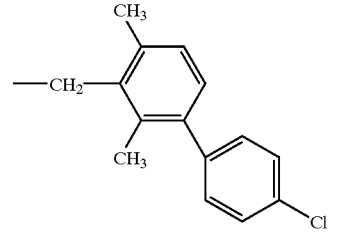 | logP = 3.43 |
| 157 | —CH₃ | —CN | —CH₃ | 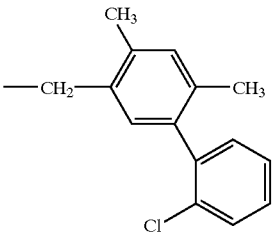 | logP = 3.24 |

TABLE 4-continued
| Ex. No. | R¹ | R² | R³ | —Y—R⁵ | Physical constant |
|---|---|---|---|---|---|
| 158 | —CH₃ | —CN | —CH₃ | 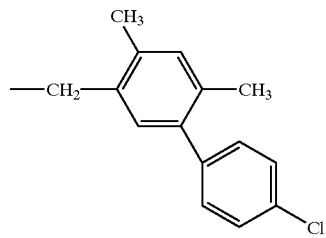 | logP = 3.49 |
| 159 | —CH₃ | —CN | —CH₃ | 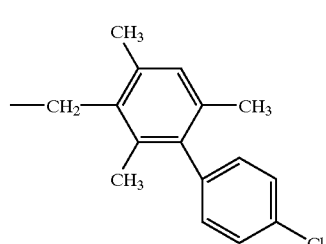 | logP = 3.70 |
| 160 | —CH₃ | —CN | —CH₃ | 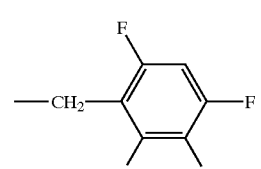 | logP = 2.32 |
| 161 | —C₂H₅ | —CN | —CH₃ | 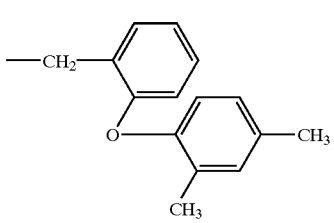 | logP = 3.44 |
| 162 | —C₂H₅ | —CN | —CH₃ | 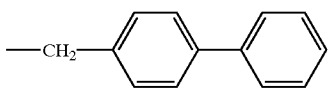 | logP = 2.81 |
| 163 | —C₂H₅ | —CN | —CH₃ | 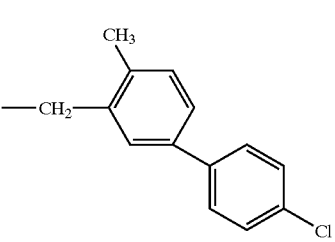 | logP = 3.49 |
| 164 | —C₂H₅ | —CN | —CH₃ | 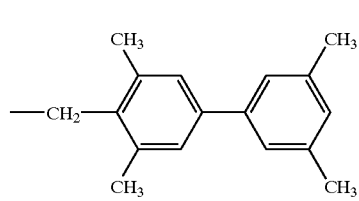 | logP = 3.96 |

TABLE 4-continued
| Ex. No. | R¹ | R² | R³ | —Y—R⁵ | Physical constant |
|---|---|---|---|---|---|
| 165 | —C₂H₅ | —CN | —CH₃ | 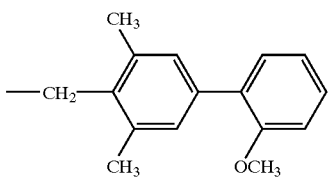 | logP = 3.20 |
| 166 | —C₂H₅ | —CN | —CH₃ | 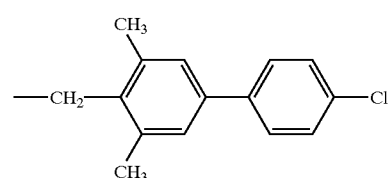 | logP = 3.74 |
| 167 | —C₂H₅ | —CN | —CH₃ | 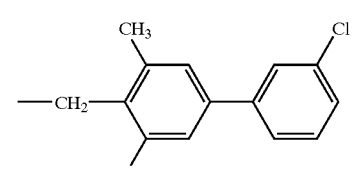 | logP = 3.70 |
| 168 | —C₂H₅ | —CN | —CH₃ | 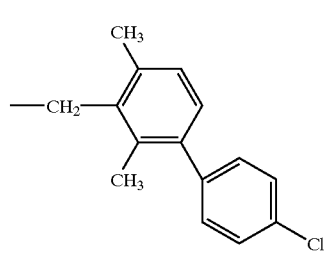 | logP = 3.71 |
| 169 | —C₂H₅ | —CN | —CH₃ | 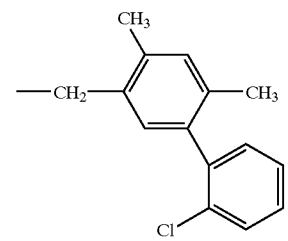 | logP = 3.51 |
| 170 | —C₂H₅ | —CN | —CH₃ | 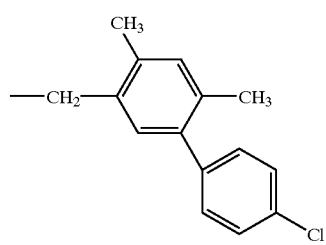 | logP = 3.77 |
| 171 | —C₂H₅ | —CN | —CH₃ | 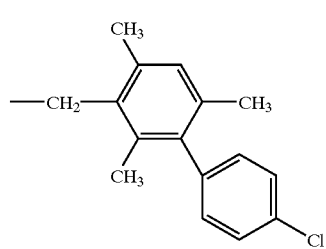 | logP = 3.98 |

TABLE 4-continued

| Ex. No. | R¹ | R² | R³ | —Y—R⁵ | Physical constant |
|---|---|---|---|---|---|
| 172 | —C₂H₅ | —CN | —CH₃ | —CH₂—(2,3,5-trifluoro-6-CF₃-phenyl) | logP = 2.59 |

USE EXAMPLES

Example A

Erysiphe Test (Wheat)/Protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of Erysiphe graminis f.sp. tritici.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

Example B

Pyrenophora Teres Test (Barley)/Curative

Solvent: 25 parts by weight of N,N-dimethylacetamide

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of Pyrenophora teres. The plants remain in an incubation cabin at 20° C. and 100% relative atmospheric humidity for 48 hours. The plants are then sprayed with the preparation of active compound at the stated application rate.

The plants are placed in a greenhouse at a temperature of about 20° C. and a relative atmospheric humidity of about 80%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE A

Erysiphe test (wheat)/protective

| Active compound | Active compound application rate in g/ha | Efficacy in % |
|---|---|---|
| According to the invention: | 250 | 100 |
| Compound (58): 1-methyl-3-ethyl-4-ethoxycarbonyl-5-[NH—C(O)—CH₂—(3-(4-chlorophenoxy)phenyl)]-pyrazole | | |

TABLE B

Pyrenophora teres test (barley)/curative

| Active compound | Active compound application rate in g/ha | Efficacy in % |
|---|---|---|
| According to the invention: 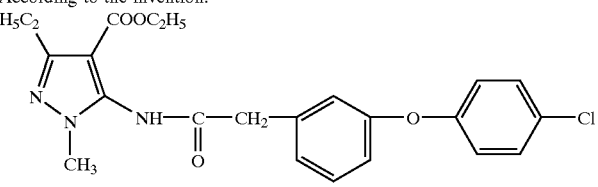 (58) | 250 | 100 |

Example C

Podosphaera Test (Apple)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen Podosphaera leucotricha. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE C

Podosphaera test (apple)/protective

| Active compound | Active compound application rate in g/ha | Efficacy in % |
|---|---|---|
| According to the invention: 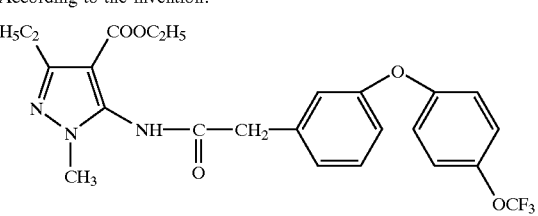 (58) | 100 | 92 |
| 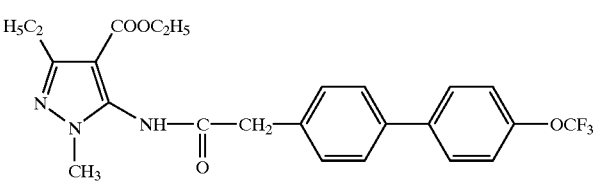 (28) | 100 | 100 |

TABLE C-continued

Podosphaera test (apple)/protective

| Active compound | Active compound application rate in g/ha | Efficacy in % |
|---|---|---|
| 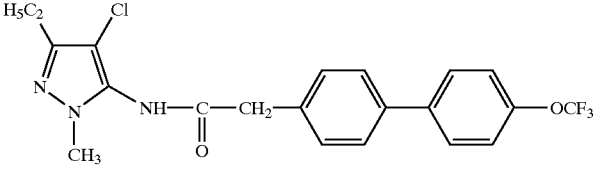 (35) | 100 | 100 |

Example D

Sphaerotheca Test (Cucumber)/Protective

Solvent: 47 parts by weight of acetone
Emulsifier: 3 parts by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Sphaerotheca fuliginea. The plants are then placed in a greenhouse at about 23° C. and a relative atmospheric humidity of about 70%.

Evalution is carried out 10 days after the inoculation. 0% means an efficacy which corresponds to that of the control, whereas an efficacy of 100% means that no infection is observed.

Active compounds, application rates and test results are shown in the table below.

TABLE D

Sphaerotheca test (cucumber)/protective

| Active compound | Active compound application rate in g/ha | Efficacy in % |
|---|---|---|
| According to the invention: 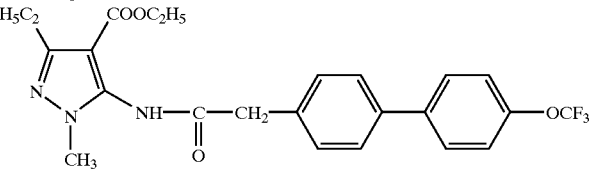 (28) | 100 | 100 |
| 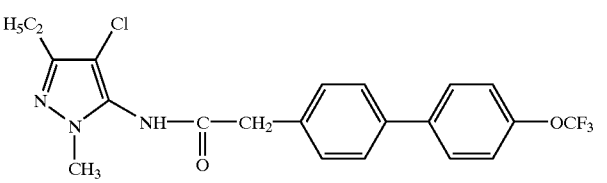 (35) | 100 | 100 |

Example E

Venturia Test (Apple)/Protective

Solvent: 47 parts by weight of acetone
Emulsifier: 3 parts by weight of alkylaryl polyglycol ether
To produce a suitable preparation of active compound, 1 part by weight of active compound is mixed with the stated amounts of solvent and emulsifier, and the concentrate is diluted with water to the desired concentration.
To test for protective activity, young plants are sprayed with the preparation of active compound at the stated application rate. After the spray coating has dried on, the plants are inoculated with an aqueous conidia suspension of the apple pathogen Venturia inaequalis and then remain in an incubation cabin at about 20° C. and 100% relative atmospheric humidity for 1 day.

The plants are then placed in the greenhouse at about 21° C. and a relative atmospheric humidity of about 90%.

Evaluation is carried out 12 days after the inoculation. 0% means an efficacy which corresponds to that of the control, whereas an efficacy of 100% means that no infection is observed.

Active compounds, application rates and test results are shown in the table below.

TABLE E

Venturia test (apple)/protective

| Active compound | Active compound application rate in g/ha | Efficacy in % |
|---|---|---|
| According to the invention: | | |
| 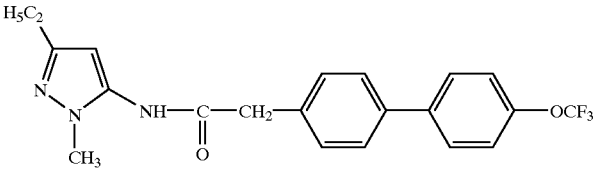 (92) | 100 | 96 |
| 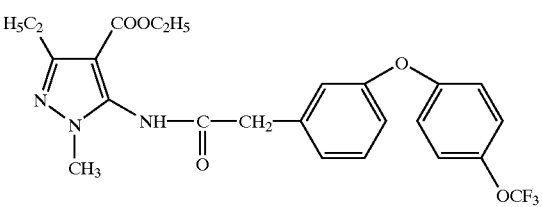 (58) | 100 | 90 |
| 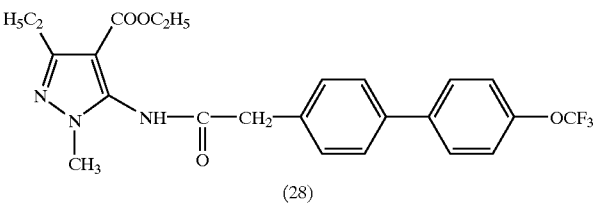 (28) | 100 | 93 |
| 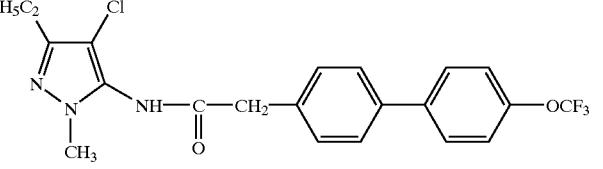 (35) | 100 | 96 |

What is claimed is:

1. A method for controlling a plant disease caused by a fungus comprising applying to said fungus and/or its locus a 5-amino-pyrazole of the formula

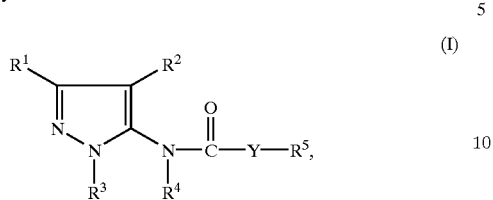

wherein

R¹ represents alkyl having 1 to 4 carbon atoms, cycloalkyl having 3 to 7 carbon atoms, alkoxyalkyl having 1 to 4 carbon atoms in the alkyl moiety and 1 to 4 carbon atoms in the alkoxy moiety or represents halogenoalkyl having 1 to 4 carbon atoms and 1 to 5 halogen atoms, R² represents hydrogen, fluorine, chlorine, bromine, cyano, nitro, trifluoromethylthio, difluoromethylthio, alkoxycarbonyl having 1 to 4 carbon atoms in the alkoxy moiety or represents alkenyloxycarbonyl having 2 to 4 carbon atoms in the alkenyloxy moiety, R³ represents optionally cyano-substituted alkyl having 1 to 4 carbon atoms or represents cycloalkyl having 3 to 6 carbon atoms which is optionally mono- to trisubstituted by substituent(s) selected from the group consisting of halogen and alkyl having 1 to 4 carbon atoms, R⁴ represents hydrogen, alkyl having 1 to 4 carbon atoms or represents cycloalkyl having 3 to 6 carbon atoms which is optionally mono- to trisubstituted by substituent(s) selected from the group consisting of halogen and alkyl having 1 to 4 carbon atoms, Y represents alkanediyl having 1 to 4 carbon atoms which is optionally mono- or disubstituted by halogen and/or cycloalkyl having 3 to 6 carbon atoms and R⁵ represents phenyl wherein the radical may be mono- to tetrasubstituted by substituent(s) selected from the group consisting of halogen, nitro, cyano, $C_1$–$C_{12}$-alkyl, $C_1$–$C_{12}$-alkoxy, $C_1$–$C_{12}$-alkylthio, $C_1$–$C_{12}$-halogenoalkyl, $C_1$–$C_{12}$-halogenoalkoxy, $C_1$–$C_{12}$-halogenoalkylthio, $C_2$–$C_{12}$-alkenyl, $C_1$–$C_4$-alkoxy-$C_2$–$C_{12}$-alkenyl, $C_1$–$C_4$-alkylthio-$C_2$–$C_{12}$-alkenyl, $C_2$–$C_{12}$-halogenoalkenyl, carboxyl, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkenyloximinoalkyl having 2 to 4 carbon atoms in the alkenyloxy moiety and 1 to 4 carbon atoms in the alkyl moiety, alkylcarbonyl having 1 to 6 carbon atoms in the alkyl moiety, alkylcarbonyloxy having 1 to 4 carbon atoms in the alkyl moiety, or by phenyl, phenoxy, phenylthio, benzyl, benzyloxy wherein the five last mentioned radicals may be mono- to trisubstituted by radical(s) selected from the group consisting of halogen, nitro, cyano, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio, or R⁵ represents phenyl wherein the radical is monosubstituted by a radical of the formula

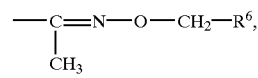

in which

R⁶ represents phenyl, which may be mono- to trisubstituted by substituent(s) selected from the group consisting of halogen, alkyl having 1 to 4 carbon atoms, halogenoalkyl having 1 to 4 carbon atoms and 1 to 5 halogen atoms and halogenoalkoxy having 1 to 4 carbon atoms and 1 to 5 halogen atoms, or R⁵ represents phenyl wherein the radical is monosubstituted by a radical of the formula

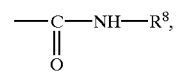

wherein

R⁸ represents alkyl having 1 to 6 carbon atoms, benzyl wherein the two last mentioned radicals may be mono- to trisubstituted by substituent(s) selected from the group consisting of halogen, alkyl having 1 to 4 carbon atoms, halogenoalkyl having 1 to 4 carbon atoms and 1 to 5 halogen atoms and halogenoalkoxy having 1 to 4 carbon atoms and 1 to 5 halogen atoms

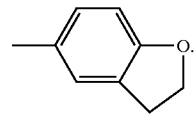

2. The method of claim 1, wherein

R¹ represents methyl, ethyl, i-propyl, tert-butyl, methoxymethyl, 1-chlorinel -ethyl, 1-fluorine-1-ethyl or cyclopropyl, R² represents hydrogen, chlorine, bromine, cyano, nitro, methoxycarbonyl, ethoxycarbonyl or allyloxycarbonyl, R³ represents methyl, ethyl, i-propyl, tert-butyl, cyclopropyl or 2-cyanoethyl, R⁴ represents hydrogen, methyl, ethyl, i-propyl or cyclopropyl, and Y represents a grouping of the formula

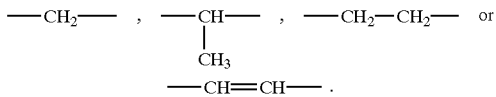

3. The method of claim 1, wherein

R⁵ represents phenyl wherein the radical is unsubstituted or mono- to trisubstituted by substituent(s) selected from the group consisting of fluorine, chlorine, bromine, nitro, cyano, methyl, ethyl, n- and i-propyl, n-, i-, s- and t-butyl, methoxy, ethoxy, n- and i-propoxy, n-, i-, s- and t-butoxy, methylthio, trifluoromethyl, trifluoromethoxy, difluoromethoxy, trifluoromethylthio, carboxyl, hydroximinomethyl, hydroximinoethyl, alkoximinoalkyl having 1 to 4 carbon atoms in the alkoxy moiety and 1 or 2 carbon atoms in the alkyl moiety, allyloximinoalkyl having 1 or 2 carbon atoms in the alkyl moiety, methylcarbonyl, ethylcarbonyl, methylcarbonyloxy, ethylcarbonyloxy, or by phenyl, phenoxy, phenylthio, benzyl, and/or benzyloxy, wherein the five last mentioned radicals are unsubstituted or mono- to trisubstituted by substituent (s) selected from the group consisting of fluorine, chlorine, bromine, nitro, cyano, methyl, tert-butyl, methylthio, methoxy, ethoxy, n- and i-propoxy, n-, i-, s- and t-butoxy, trifluoromethyl, trifluoromethoxy, difluoromethoxy and trifluoromethylthio.

4. The method of claim 1, wherein $R^5$ represents phenyl wherein the radical is unsubstituted or mono- to trisubstituted by substituent(s) selected from the group consisting of fluorine, chlorine, bromine, nitro, cyano, methyl, ethyl, n- and i-propyl, n-, i-, s- and t-butyl, methoxy, ethoxy, n- and i-propoxy, n-, i-, s- and t-butoxy, methylthio, trifluoromethyl, trifluoromethoxy, difluoromethoxy, trifluoromethylthio, carboxyl, hydroximinomethyl, hydroximinoethyl, alkoximinoalkyl having 1 to 4 carbon atoms in the alkoxy moiety and 1 or 2 carbon atoms in the alkyl moiety, allyloximinoalkyl having 1 or 2 carbon atoms in the alkyl moiety, methylcarbonyl, ethylcarbonyl, methylcarbonyloxy, ethylcarbonyloxy.

5. A method according to claim 1, wherein $R^5$ represents phenyl wherein the radical is monosubstituted by a radical of the formula

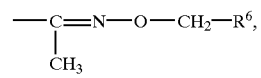

wherein $R^6$ represents phenyl, where each of these radicals are unsubstituted mono- to trisubstituted by identical or different substituents from the group consisting of fluorine, chlorine, bromine, methyl, ethyl, trifluoromethyl and trifluoromethoxy.

6. The method of claim 1, wherein $R^5$ represents phenyl wherein the radical monosubstituted by a radical of the formula

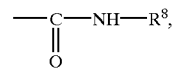

wherein $R^8$ represents methyl, ethyl, n-propyl or benzyl, wherein the last mentioned radical is unsubstituted or mono- to trisubstituted by substituent(s) selected from the group consisting of fluorine, chlorine, bromine, methyl, ethyl, n-propyl, trifluoromethyl and trifluoromethoxy.

* * * * *